(12) United States Patent
Klemic et al.

(10) Patent No.: US 6,699,697 B2
(45) Date of Patent: Mar. 2, 2004

(54) PLANAR PATCH CLAMP ELECTRODES

(75) Inventors: Kathryn G. Klemic, New Haven, CT (US); James F. Klemic, New Haven, CT (US); Mark A. Reed, Monroe, CT (US); Frederick J. Sigworth, Hamden, CT (US)

(73) Assignee: Yale University, New Haven, CT (US)

( * ) Notice: Subject to any disclaimer, the term of this patent is extended or adjusted under 35 U.S.C. 154(b) by 216 days.

(21) Appl. No.: 09/780,630

(22) Filed: Feb. 12, 2001

(65) Prior Publication Data

US 2002/0064841 A1 May 30, 2002

Related U.S. Application Data

(60) Provisional application No. 60/181,935, filed on Feb. 11, 2000.

(51) Int. Cl.$^7$ ............................................... C12N 13/00
(52) U.S. Cl. ............................... 435/173.4; 435/173.5; 435/173.6; 435/287.1; 435/288.4; 204/280; 204/403.1
(58) Field of Search ........................ 435/173.4, 173.5, 435/173.6, 285.2, 287.1, 288.4; 204/403.1, 280

(56) References Cited

U.S. PATENT DOCUMENTS

| | | | |
|---|---|---|---|
| 5,981,268 A | 11/1999 | Kovacs et al. | 435/287.1 |
| 6,020,047 A | 2/2000 | Everhart | 428/209 |
| 6,048,722 A | 4/2000 | Farb et al. | 435/287.1 |
| 6,368,851 B1 * | 4/2002 | Baumann et al. | 435/285.2 |
| 6,379,916 B1 * | 4/2002 | Meyer | 435/29 |
| 2002/0006357 A1 * | 1/2002 | McGeoch et al. | 422/82.01 |
| 2002/0104757 A1 * | 8/2002 | Schmidt | 204/418 |

FOREIGN PATENT DOCUMENTS

| | | | |
|---|---|---|---|
| JP | 4338240 | 5/1991 | |
| WO | WO 94/25862 | 11/1994 | G01N/27/33 |
| WO | WO 97/45730 | 12/1997 | G01N/33/50 |
| WO | WO 98/50791 | 11/1998 | G01N/33/483 |
| WO | WO 99/31503 | 6/1999 | G01N/33/487 |

OTHER PUBLICATIONS

Byfield et al., 1994, Biosensors & Bioelectronics, 9: 373–400.
Duffy et al., 1998, Analytical Chemistry 70: 4974–4984.
Green, 1989, Modern Plastics Encyclopedia, p. 270–272.
Hammill et al., 1981, Pflugers Arch., 391: 85–100.
International Search Report mailed Jul. 24, 2001.
Kim et al., 1995, Nature, 376: 581–584.
Klemic et al., 2000, Biophysical Journal, 78: 266A (Abstract).
Levis et al., 1993, Biophy. J., 65: 1666–1677.
Lowe, 1984, Trends in Biotechnology, 2: 59–65.
Parker, 1989, Modern Plastics Encyclopedia, p. 264–268.
Schmidt et al., 2000, Angew. Chem. Int. Ed., 39: 3137–3140.
Sigworth, 1986, Fed. Proc. 45(12): 2673–2677.
Sigworth et al., 1995, J. Neurosci Methods, 56: 203–215.
Xia et al., 1996, Science, 273: 347–349.
Xia et al., 1998, Angew. Chem. Int. Ed., 37: 550–575.

* cited by examiner

*Primary Examiner*—David A. Redding
(74) *Attorney, Agent, or Firm*—Morgan, Lewis & Bockius LLP

(57) ABSTRACT

The present invention relates to ionic electrodes, particularly microelectrodes and electrode arrays, and also relates to fabrication methods for such electrodes. In particular, the present invention relates to planar polymer electrodes for making patch clamp measurements of ionic currents through biological membranes, such as the plasma membranes of living cells. The electrodes of the present invention are useful for measuring individual and multisite cell membrane currents and voltages, as well as in high-throughput screening procedures.

27 Claims, 12 Drawing Sheets

PDMS patch electrode & associated components, side view

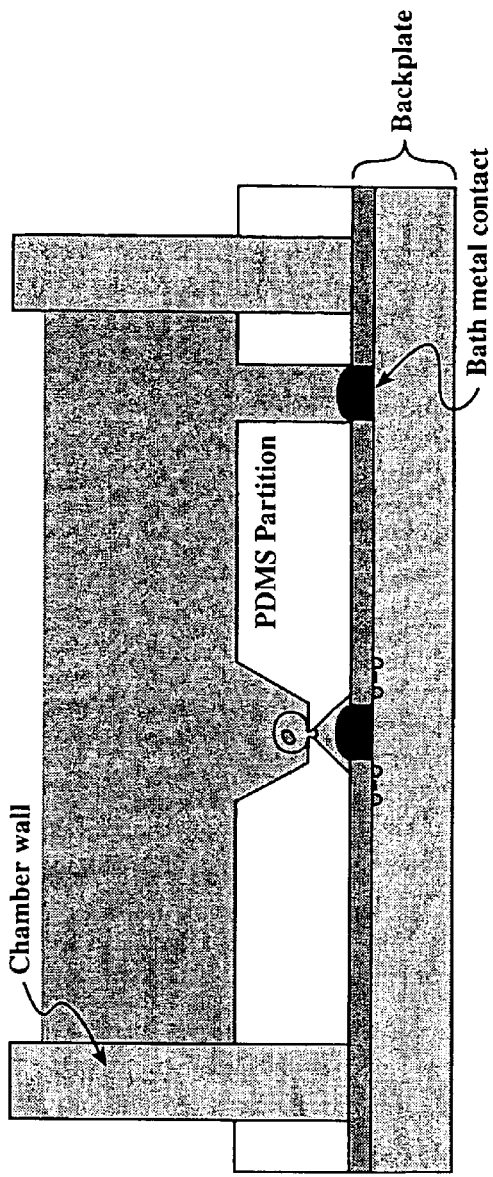
Fig. 1A  PDMS patch electrode & associated components, side view
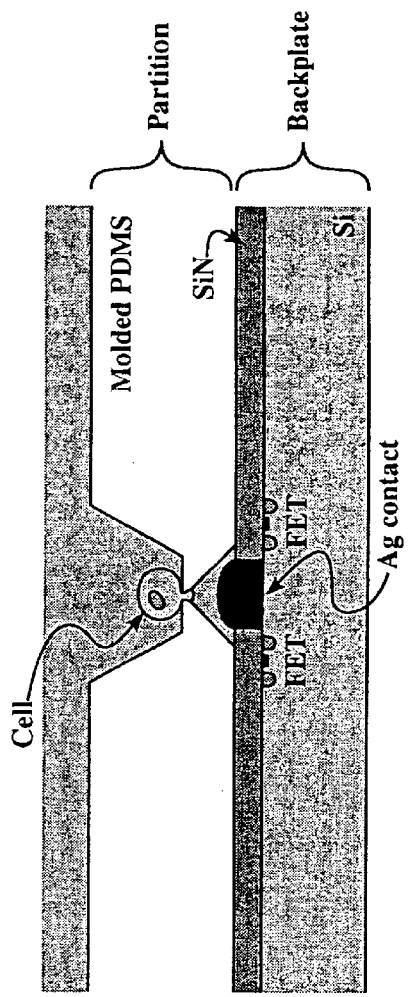
Fig. 1B  PDMS patch electrode, side view

Close-up of cell contact point to partition

Alternative PDMS patch electrode, side view

Top view of a 96 well plate, 16 patch electrodes/well

Side view of patch electrode array in a single well

Alternative patch electrode array, including microfluidic solution exchange valves Electronic circuitry for a single well Shaker K+ channel current recording from *Xenopus* oocyte sealed to planar PDMS patch electrode Process flow chart
for micromolding PDMS electrode
partition from a micromachined Si master PDMS patch electrode array system PDMS patch electrode array system, including fluidic layer

PLANAR PATCH CLAMP ELECTRODES

CROSS REFERENCE TO RELATED APPLICATION

This application claims priority of U.S. Provisional Patent Applications 60/181,935 filed Feb. 11, 2000 which is herein incorporated by reference in its entirety.

STATEMENT OF RIGHTS TO INVENTIONS MADE UNDER FEDERALLY SPONSORED RESEARCH

This invention was partially made with government support under NIH/NCRR Grant No. RR12246, NINDS Grant No. NS21501 and ONR Grant No. N00014-99-1-0406.

FIELD OF THE INVENTION

The present invention relates generally to biosensors, including methods of making biosensors and methods of measuring cellular signal transduction processes using biosensors. More specifically, the present invention relates to ionic electrodes, particularly microelectrodes and electrode arrays, and also relates to fabrication methods for such electrodes and to methods of using such electrodes. More particularly, the present invention relates to planar silicone polymer electrodes for making patch clamp measurements of ionic currents through biological membranes, such as the plasma membranes of living cells, as well as to methods of making and utilizing such electrodes. The biosensor apparatus and methodology of the present invention provide for the high-throughput measurement of ionic currents through biological membranes. The biosensors of the present invention are particularly useful for screening new drugs that act on cell-membrane ion channels and transporters.

BACKGROUND OF THE INVENTION

All publications, patents and patent applications herein are incorporated by reference to the same extent as if each individual publication, patent or patent application was specifically and individually indicated to be incorporated by reference.

Many cellular processes are controlled by changes in cell membrane potential due to the action of ion channels. Action potentials trigger the release of hormones and neurotransmitters in secretory cells and neurons; they trigger contractions in muscle cells and influence biochemical events and levels of gene expression. Action potentials and other changes of membrane potential are in turn triggered by the opening of ion channels that are coupled to receptors for neurotransmitters or intracellular messengers, or by ion channels that are mechanosensitive or voltage-sensitive. The wide variety of ion channels arises from large families of genes and represents a rich collection of new targets for pharmaceutical agents.

The patch clamp technique is the central technique for studying ion channels. It provides a "voltage clamp" measurement of ionic current in either a small "patch" of cell membrane, or the entire membrane of a small cell. Because it is a measurement of current, it directly monitors the number of active channels in the membrane, and is therefore the assay of choice for agents that block or modulate channel activity. It is also the only reliable way to make electrical recording from small cells, such as neurons and most other cells in vertebrate animals. Its development was recognized by the Nobel Prize in 1991, which was awarded to E. Neher and B. Sakmann. For general introductions, see Boulton et al.(Editors), *Patch Clamp Applications and Protocols*, Humana Press (1995); Neher and Sakmann (Editors), *Single-Channel Recording*, Plenum Press (1995), and DeFelice, *Electrical Properties of Cells: Patch Clamp for Biologists* (The Language of Science), Plenum Pub. Corp. (1997), each of which is specifically incorporated by reference in its entirety.

Fundamentally, an electrode for patch clamp recording consists of an insulating partition that separates the cell and its surrounding "bath" solution, on one side, from a compartment filled with ionic solution and containing a nonpolarizable electrically conducting contact, typically a silver wire with a silver-chloride (AgCl) surface coating. A small aperture in this partition defines a region from which current is measured. A conventional patch clamp electrode consists of a saline-filled glass micropipette, having a tip opening of roughly one micron, which is pressed against the cell membrane. The pipette's tip comprises the electrode partition; with the AgCl coated silver wire inserted into the back end of the pipette, the pipette collects ionic current passing through the membrane patch covered by the tip, allowing "patch" recording. In the alternative, "whole-cell recording" configuration, the membrane patch is ruptured, giving direct electrical access to the cell interior. The current collected by the patch electrode ranges in magnitude from roughly one picoampere (for currents of individual channels in the membrane patch) to tens of nanoamperes (in the case of large whole-cell currents). The current is monitored by a sensitive preamplifier that is located close to the pipette and is connected to the AgCl coated silver wire.

Conventionally, glass micropipettes act as electrode partitions and are fabricated in the user's laboratory within a few hours of their use. The fabrication consists of three steps. First, a glass or quartz capillary tube (about 1.5 mm diameter) is heated at its center while the ends are pulled slowly by carefully moving it until the tube breaks into two pieces. Each has a tapered shank leading to a tip opening of a few microns. In a second, optional, step, the shank of the pipette is coated with a hydrophobic material such as wax or a silicone elastomer to decrease the total electrical capacitance of the patch electrode; care is taken so that the coating does not approach the tip opening, where it may prevent sealing to the cell membrane. Lastly, the tip is "heat-polished" by carefully moving it closely to a heated filament to round the edges and establish the final tip diameter of roughly one micron.

The patch electrode is filled with an ionic solution that is typically chosen to mimic the extracellular fluid, and is mounted onto a holder that is attached directly to a preamplifier, which in turn is mounted on a three-axis micromanipulator. Viewing a petri dish of cells through an inverted microscope, the operator uses the micromanipulator to position the pipette tip to touch the membrane of a chosen cell. Gentle suction is applied to the pipette interior to draw the cell membrane toward the tip, and under favorable conditions a mechanically stable, high-resistance seal (>1 gigaohm) spontaneously occurs between the membrane and the clean glass surface of the tip. Once the seal is established, the voltage of the membrane can be set according to the experimental goals and currents are recorded through the use of the preamplifier and its associated main amplifier. Examples of commercial patch clamp amplifiers include the AxoPatch 200 series by Axon Instruments, Inc. and the EPC series by HEKA Elektronik.

The present invention improves the instrumentation used to study membrane proteins, especially the study of ion channels. This is important for the advancement of basic research in this area as well as for high-throughput screening of pharmacological agents acting on these proteins.

Several attempts have been made to improve the reliability, reproducibility and overall throughput capacity of conventional glass patch clamp readings. For example, WO 98/50791 discloses a fully automated pipette patch clamp technique which provides computer aided guiding of the pipette to the cell. While this method is useful, it only provides for measuring one cell at a time and connecting the cell and the pipette is difficult. WO 99/31503 discloses a glass patch electrode with an electrically charged surface which provides for more precise positioning of biological membranes on the electrode surface. U.S. Pat. No. 6,048, 722 combines a glass patch electrode with an automatic perfusion system connected to a recording chamber, permitting cells to be perfused with a plurality of solutions containing different concentrations of one or more agents to be tested. JP 4338240 discloses treating the surface of a glass micro-pipette in oxygen plasma to improve the ability of the glass surface to seal against biological membranes.

The present invention greatly improves the "ease of use" of patch clamp recording of membrane ion currents and increases the overall throughput of data collection, especially for drug discovery and research purposes. In addition, the present invention permits simple exchange of the electrode chamber solution. The novel patch electrodes of the present invention allow a better signal-to-noise ratio for high-resolution recording of membrane currents or voltage and higher spatial resolution and mapping.

The present invention allows fabrication by micromolding so that many electrode partitions can be fabricated simultaneously, as a patch electrode array. In addition the micromolding methods of the present invention have low manufactururing costs making the partition disposable so as to avoid rigorous cleaning between use.

For commercial applications, the present invention permits a direct assay of ion channel activity in the presence of pharmaceutical agents in a simple and highly-parallel fashion. Presently, a first and second level of screening of agents is done by indirect measures of ionic current as reported by radiotracer fluxes or fluorescent dyes. The present invention greatly improves the accuracy and throughput of screening so that pharmaceutical effects may be assayed directly from the target molecules in the initial screening steps of the drug discovery process.

The embodiments and advantages of this invention are set forth, in part, in the description and examples which follow and, in part, will be obvious from this description and examples and may be further realized from practicing the invention as disclosed herein.

SUMMARY OF THE INVENTION

The present invention is based, in part, on the discovery that polymeric materials may be treated in order to provide a high-resistance seal for patch electrodes used to measure electrical currents or voltages across/through biological membranes. The invention is further based on the discovery that such patch electrodes may be mass produced by appropriate molding techniques for disposable use, and that the molded structure can be integrated with an electronic backplate containing the amplifier electronics to form a biosensor chip. Based on these discoveries, the present invention provides compositions and methods for use in patch clamp recording after surface modification of the polymeric surface.

The present invention provides electrodes comprising a silicone polymer molded so as to form a partition comprising an aperture, said apertured-partition capable of forming a high resistance seal of at least 100 MΩ with a biological membrane; and a backplate associated with the apertured-partition, said backplate comprising an electrically conductive contact, wherein the association of the apertured-partition and the backplate forms a compartment associated with the aperture, and wherein the said compartment contains the electrically conductive contact.

The present invention further provides such electrodes which include walls associated with the electrodes so as to form chambers.

The present invention provides apparatus for measuring ionic currents through a biological membrane, wherein the apparatus comprises:
a). electrodes comprising:
  i). a silicone polymer molded so as to form a partition comprising an aperture, said apertured-partition capable of forming a high resistance seal of at least 100 MΩ with a biological membrane; and
  ii). a backplate associated with the apertured-partition, said backplate comprising an electrically conductive contact, wherein the association of the apertured-partition and the backplate forms a first compartment associated with the aperture, and wherein the said first compartment contains the electrically conductive contact and a first solution; and
b). walls associated with the electrodes so as to form chambers, said chambers comprising a second compartment containing a second solution.

The present invention further provides such apparatus wherein the first and second solution is the same. Alternatively, the invention also provides such apparatus wherein the first and second solution is different.

The present invention also provides such apparatus further comprising a switching circuit associated with the electrically conductive contact. The present invention further provides such apparatus comprising an amplifier associated with the electrically conductive contact. The present invention even further provides such apparatus further comprising a recording means. In some preferred embodiments, the apparatus of the present invention include recording means selected from the group consisting of a digital recorder, a computer, volatile memory, involatile memory, chart recorder, and combinations thereof.

The present invention also provides electrodes as discussed above wherein the surface of the silicone polymer adjoining the aperture has been oxidized.

The present invention further provides such electrodes wherein the size of the aperture varies from about 0.1 micron to about 100 microns. In some preferred embodiments, the electrodes of the present invention have an aperture size which can vary from about 1 micron to about 20 microns. In some preferred embodiments, the electrodes of the present invention have an aperture size which can vary from about 1 micron to about 10 microns. In some preferred embodiments, the electrodes of the present invention have an aperture size which varies from 1 micron to about 2 microns.

The present invention further provides electrodes as described above wherein the silicone polymer is polydimethylsiloxane (PDMS).

The present invention also provides such electrodes which also include one or more supportive structures associated with the partition.

The present invention also provides such electrodes which include one or more microfluidic channels associated with the backplate. In some embodiments, the electrodes of the present invention include one or more microfluidic channels incorporated into a poly-dimethylsiloxane layer of the backplate. In some preferred embodiments, the electrodes of the present invention include one or more microfluidic channels fabricated into the backplate.

The present invention also provides such electrodes which include one or more microfluidic valves associated with the backplate. In some preferred embodiments, the electrodes of the present invention include one or more microfluidic valves incorporated into a poly-dimethylsiloxane layer of the backplate. In some preferred embodiments, the electrodes of the present invention include one or more microfluidic valves fabricated into the backplate. Such microfluidic valves may be in addition to one or more microfluidic channels.

The present invention provides the apparatus discussed above wherein the biological membrane used to obtain the measurements is part of a cell.

The present invention further provides the apparatus discussed above which additional includes a removable cover.

The present invention provides multiple electrode arrays which include a plurality of electrodes according to this invention, wherein the electrodes are within one or more wells. In some preferred embodiments, the multiple electrode arrays of the present invention comprise 96, 384 or 1536 wells.

The present invention provides methods of measuring cell membrane currents or cell voltages comprising:

a). sealing one or more cells to an apertured-partition of an apparatus used for measuring ionic currents across a biological membrane, said apparatus comprising:

i). an electrode comprising a silicone polymer molded so as to form a partition comprising an aperture, said apertured-partition capable of forming a high resistance seal of at least 100 MΩ with a biological membrane; and a backplate associated with the apertured-partition, said backplate comprising an electrically conductive contact, wherein the association of the apertured-partition and the backplate forms a first compartment associated with the aperture, said first compartment containing the electrically conductive contact and a first solution; and ii). walls associated with the electrode so as to form a chamber, said chamber comprising a second compartment containing a second solution; and b). measuring the cell membrane currents or cell voltages of the one or more cells sealed to the apertured-partition.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown.

FIG. 1a. PDMS patch electrode and associated components, side view. This figure depicts a partial cut-away view of a basic patch clamp electrode and associated components according to the present invention.

FIG. 1b. PDMS patch electrode, side view. This figure depicts a close up of a partial cut-away view of a basic patch clamp electrode according to the present invention. The area designated "Si" is the electronic chip comprising a silicon substrate which contains the field-effect transistors ("FETS"). The Si layer is covered by a thin nitride layer, SiN, that insulates the electronics from the ionic solutions. The Si and SiN layers together constitute the backplate in this example. The solution surrounding the cell is the bath solution. A small amount of electrode solution is sealed in when the partition, composed of molded PDMS, and the backplate come into in contact.

A cell is placed over the small aperture of the partition and a small amount of suction may be drawn to seal the cell to the partition. In this way, the partition seals onto the electronic chip directly. The aperture is from about 0.1 micron to about 100 microns in size.

Figure 3:
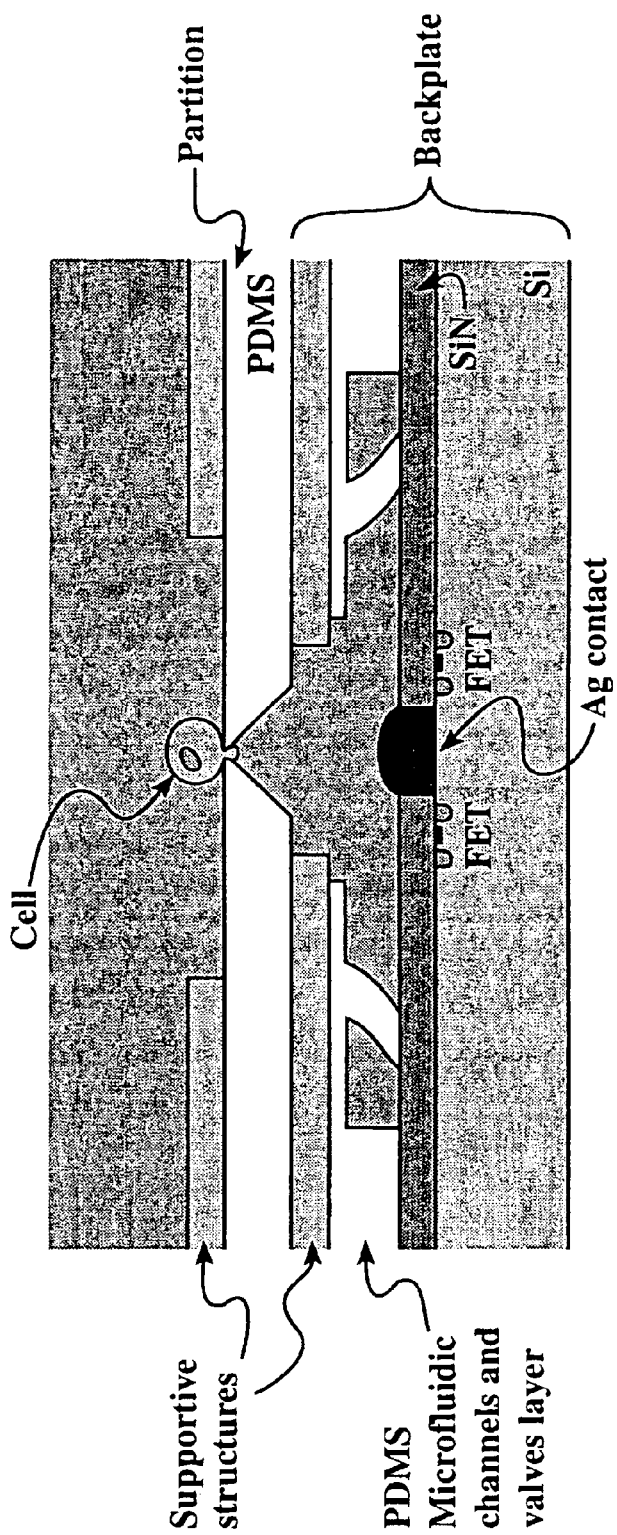

FIG. 3. Alternative PDMS patch electrode, side view. This figure depicts an alternative configuration for a patch clamp electrode according to the present invention.

In this alternative configuration, two separate sheets of polymer are molded. One contains the shape of the small aperture at the cell interface and the other contains microfluidic channels and valves. These polymer layers are sandwiched together with a supportive structures as shown in FIG. 1. In this example, the backplate comprises a supportive structure, a PDMS layer with microfluidic channels and valves, a SiN layer, a Si substrate, an electrically conducting contact (e.g., a Ag contact), and two FETs.

This configuration could alternatively have a single PDMS sheet containing both the cell interface aperture and the microfluidic channels and/or valves, with or without supportive structures.

Figure 4:
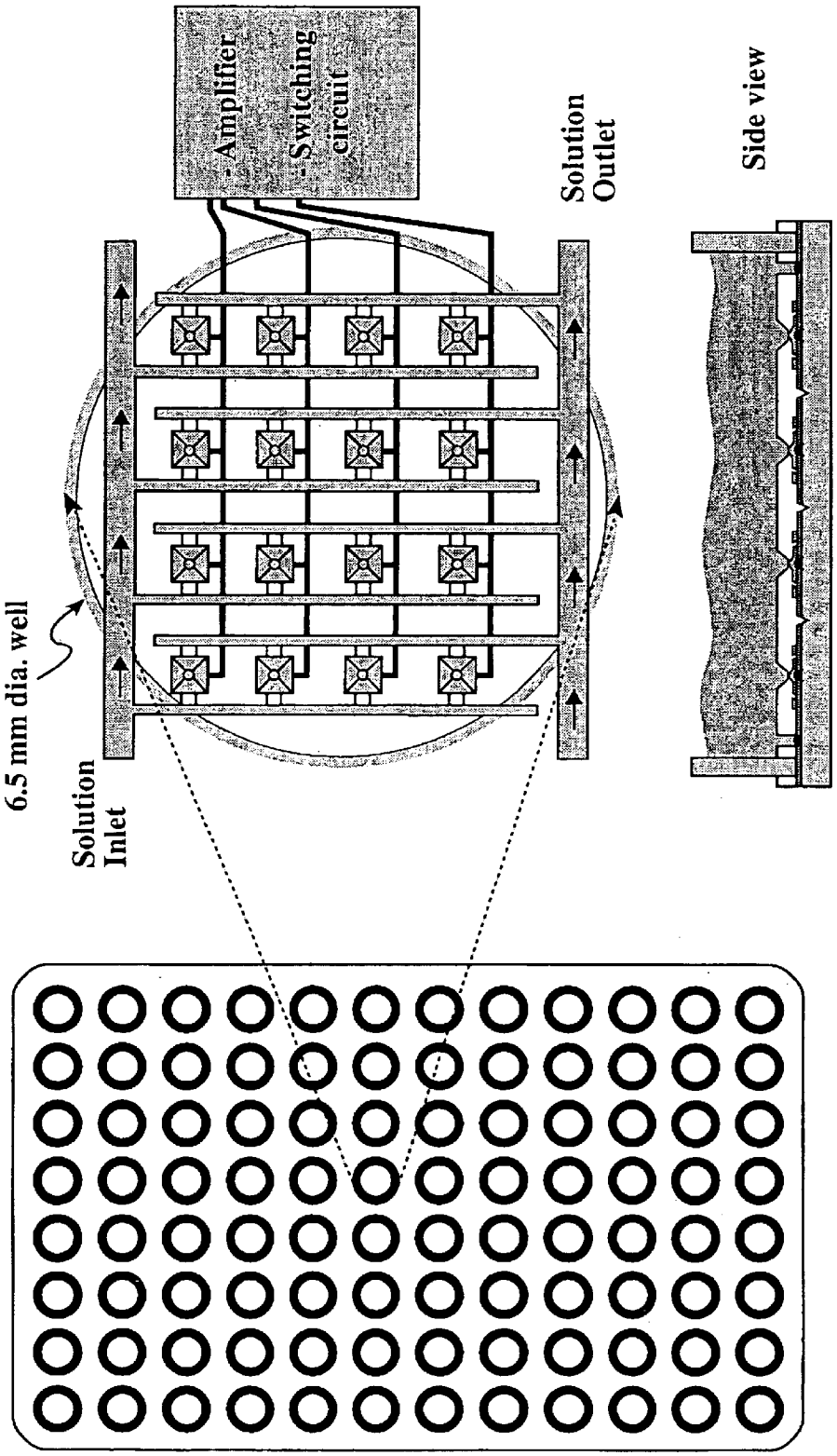

FIG. 4. Top view of a 96 well plate, 16 patch electrodes/well. This figure illustrates a standard, 96 well microtiter plate that has been equipped with a patch electrode array according to the present invention.

The figure shows a top view of a 96 well plate with a zoom-view into a single well. Essentially a bottomless 96 well plate is pressed onto the partition structure that has 96—4×4 arrays of patch electrodes, for a total of 1536 patch electrodes.

Different configurations are also encompassed by this invention. For example, the patch electrode array may have 1, 2, 4 or 16 apertures per well in a 96, 384 or 1536 well plate.

Figure 5:
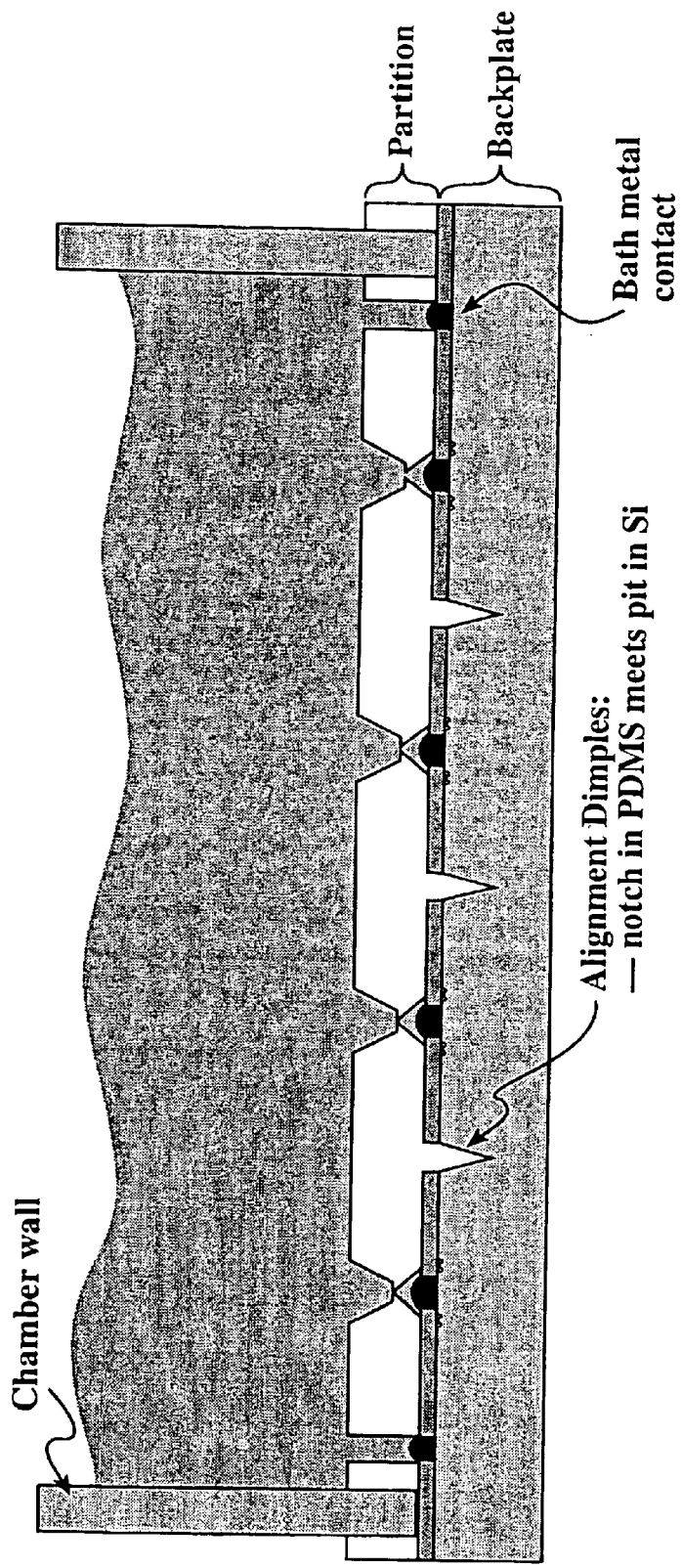

FIG. 5. Side view of patch electrode array in a single well. This figure depicts a schematic diagram of a multiple patch electrode array according to the present invention.

The figure illustrates a cut-away view of a 4×4 array of patch electrodes, such patch electrodes being described in FIG. 1. Silver-chloride (AgCl) coated silver contacts exposed to the bath solution connects to the ground of the amplifier. The wall of the chamber acts to hold the polymer sheet in place. Several dimples are included in the molded structure that align precisely with etched pits in the backplate to position each aperture to the appropriate AgCl coated silver contact.

Figure 6:
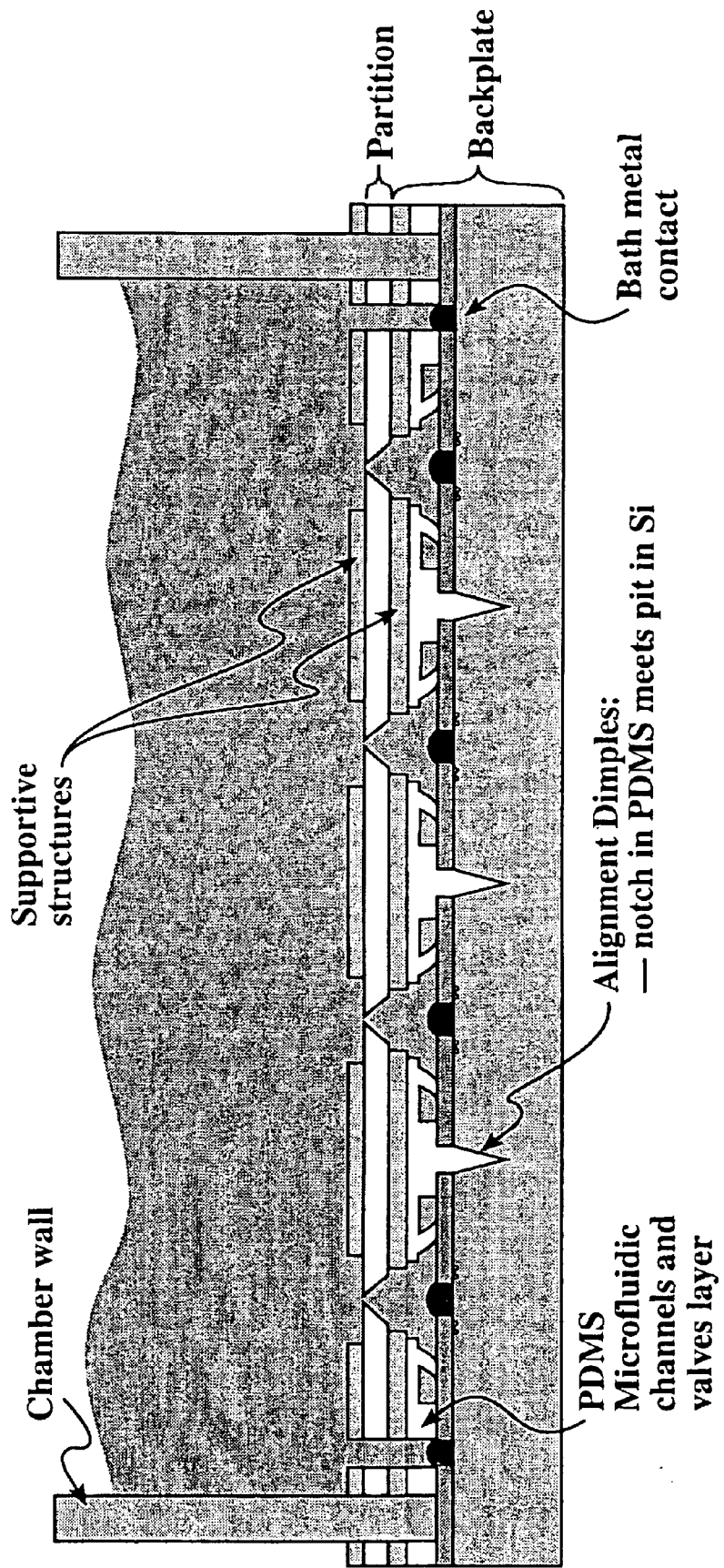

FIG. 6. Alternative patch electrode array, including microfluidic solution exchange valves. This figure depicts another configuration for an array of patch clamp electrodes according to the present invention, including optional supporting structures and microfluidic channels and valves.

The figure illustrates a cut-away view of a 4×4 array of patch electrodes, such patch electrodes being described in FIG. 3. The supportive structures align with the chamber wall for correct positioning.

Figure 7:
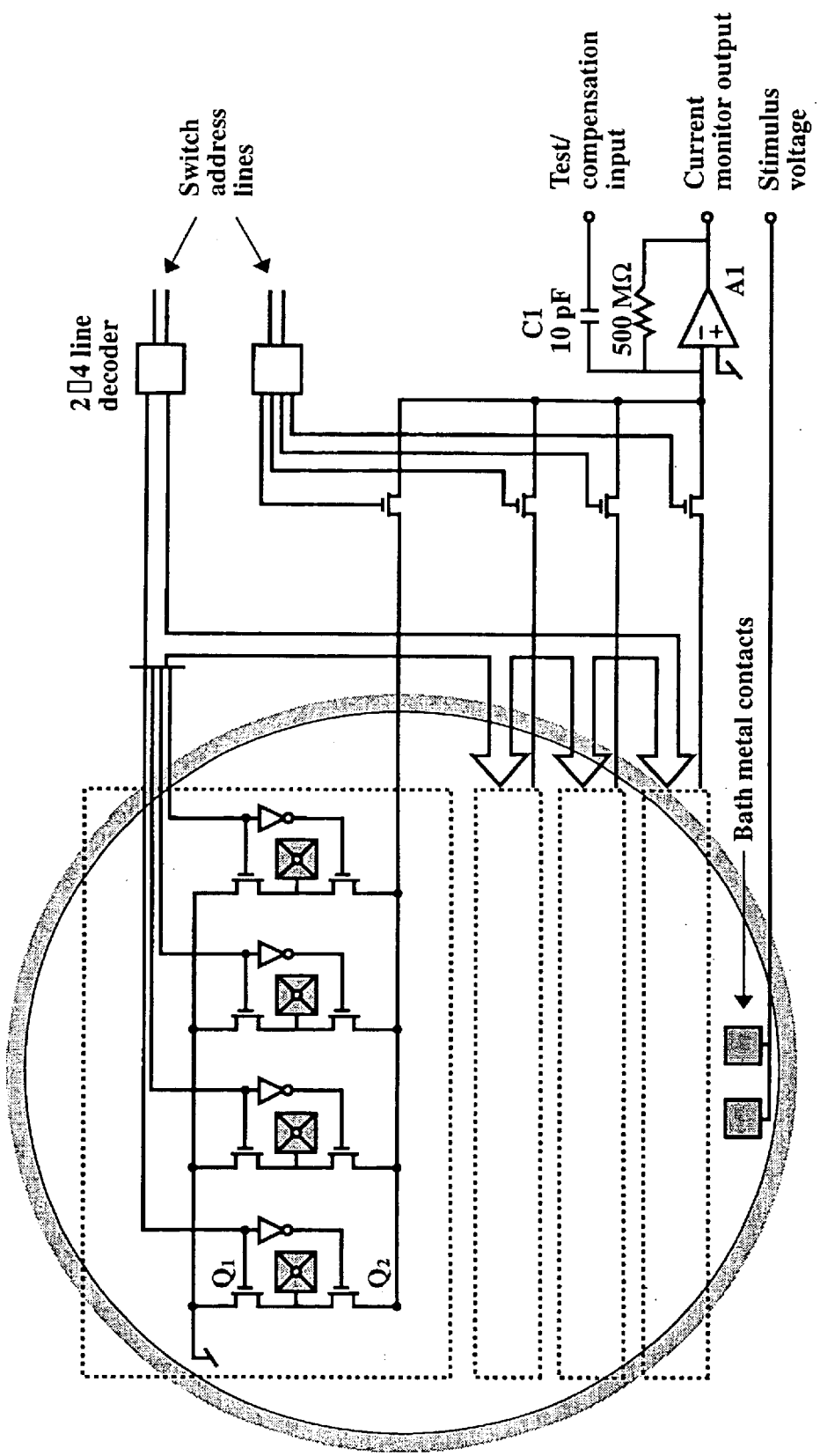

FIG. 7. Electronic circuitry for a single well. This figure illustrates an example of the electrode switching and preamplifier circuit of the present invention. Each electrically conducting contact (e.g., metal contact) is connected to two switching transistors Q1 and Q2. If the electrode is "off" it is connected through Q1 to ground; if it is "on" it is connected through Q2 to the input of the current-to-voltage (I-V) converter. A digital decoder allows selection of a single electrode to be "on" at a given time. The I-V converter consists of operational amplifier A1 and a feedback element (in this example, a 500 MΩ resistor). A capacitor C1 serves to inject currents into the I-V converter for test purposes, or, with an appropriately conditioned voltage applied, to compensate for capacitive currents.

Figure 8:
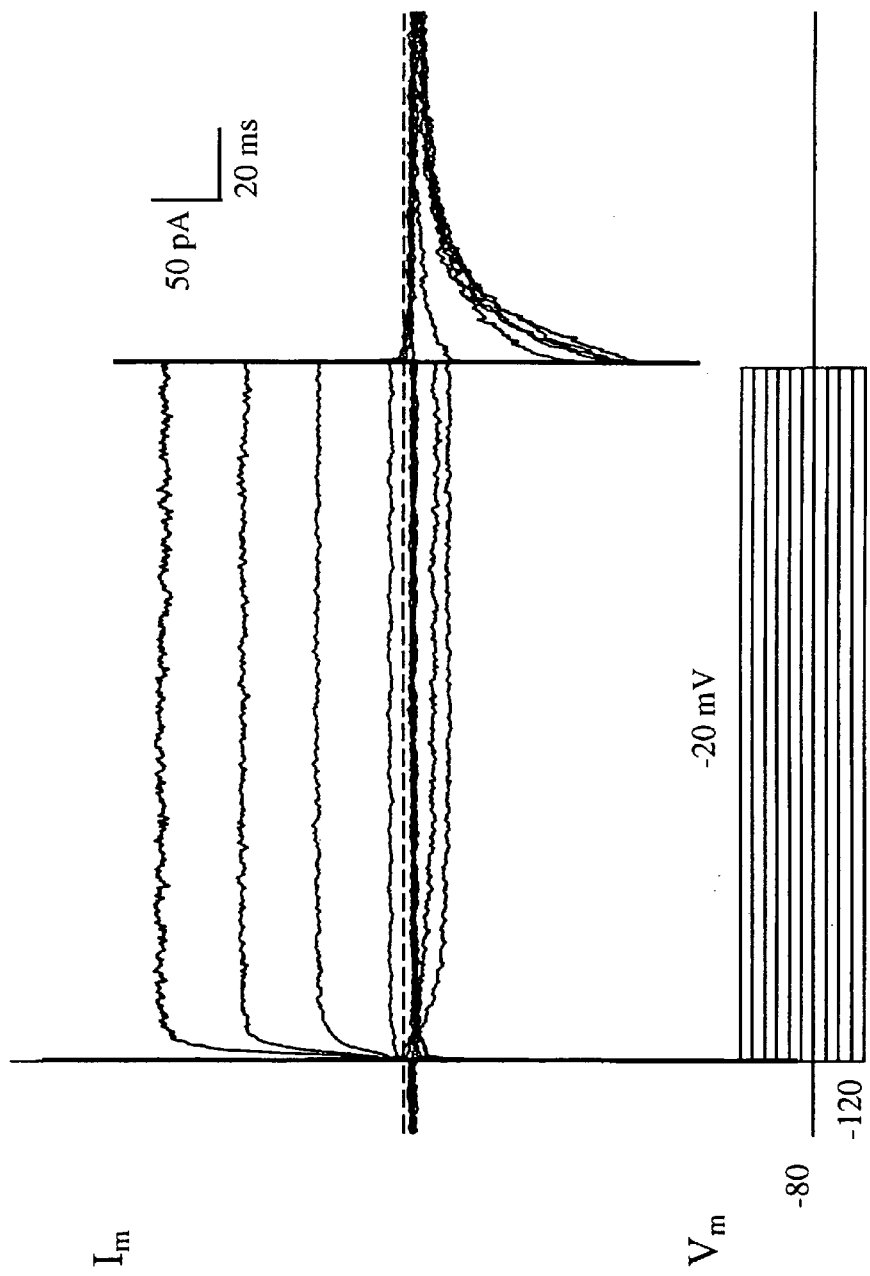

FIG. 8. Shaker K+ channel current recording from Xenopus oocyte sealed to planar PDMS patch electrode. This figure shows the data recorded from a Xenopus oocyte sealed to the planar PDMS patch electrode.

A Xenopus oocyte expressing the Shaker potassium channel was placed onto an 8 micron hole in the planar PDMS sheet, as described in Example 8. Once a high resistance seal (>4GΩ) was established, the membrane potential of the patch was held at −80 mV. The membrane current (Im) was recorded while the membrane potential (Vm) was stepped to a new potential for 200 ms then returned to −80 mV. The family of current traces, Im, are the current records during successive step changes in membrane potential, from −120 to −20 mV in 10 mV increments. The current was sampled at 20 kHz and filtered at 2 kHz.

Figure 9:
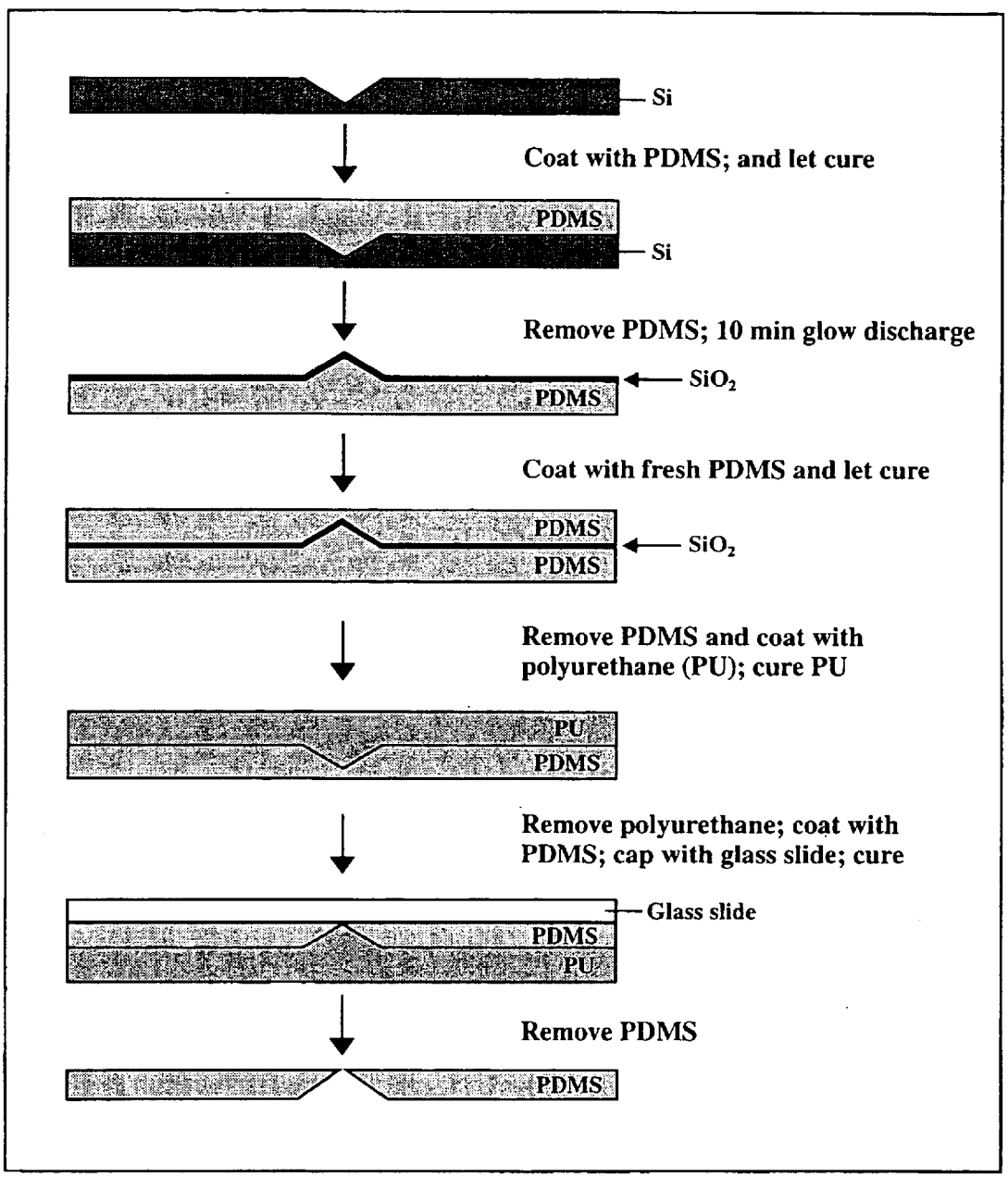

FIG. 9. Process flow chart for micromolding PDMS electrode partition from a micromachined Si master. This figure depicts a process flow for fabrication of a PDMS partition. Starting with a silicon master, two PDMS molding steps result in a replica containing pyramidal pits. A subsequent molding step with polyurethane results in a structure with raised pyramids, which serves as the final mold for the PDMS partition.

Figure 10:
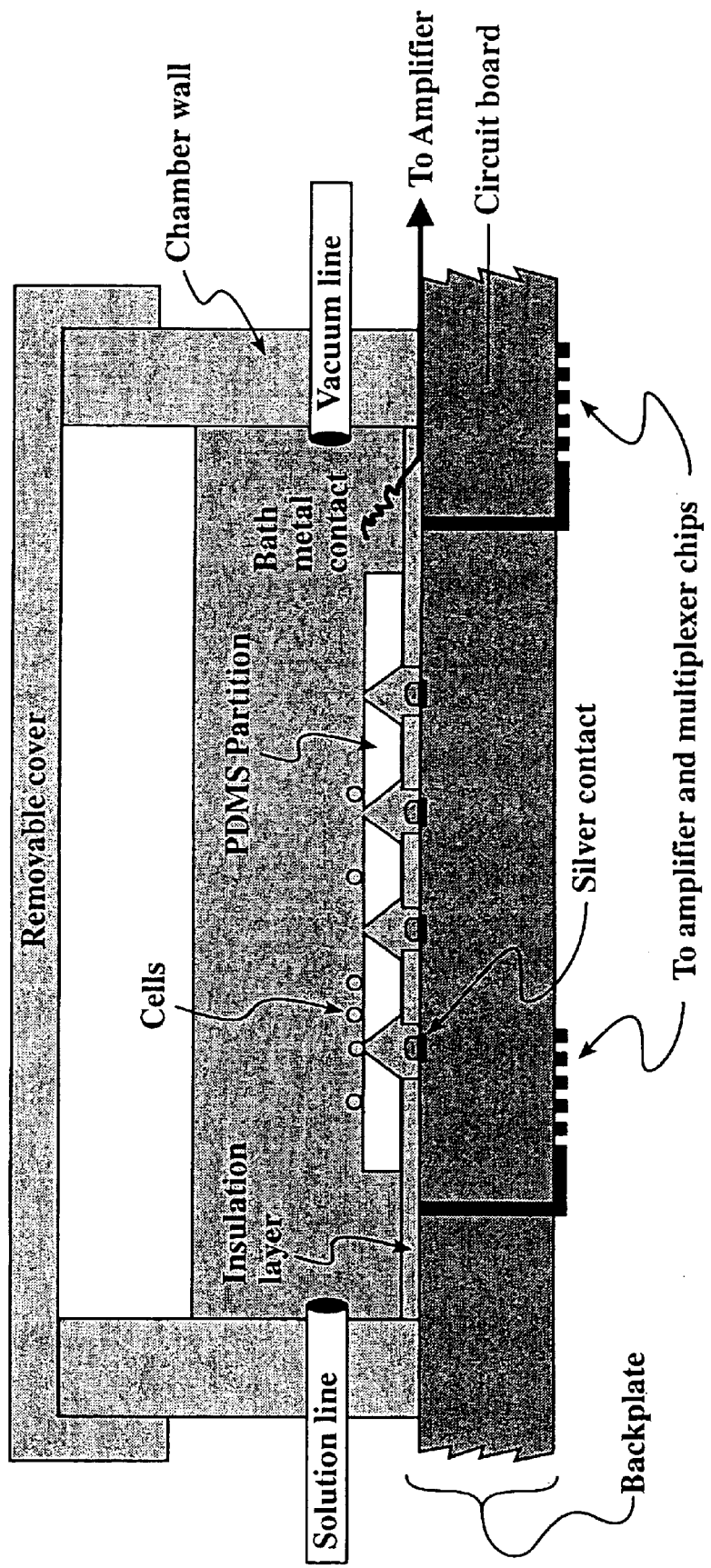

FIG. 10. PDMS patch electrode array system. This figure depicts an example of a PDMS patch electrode array system. The backplate consists of a glass-epoxy printed-circuit board with a PDMS insulation layer attached. Plated through-holes in the circuit board provide electrical connection between silver contacts on the top surface of the backplate and lines leading to the multiplexer and amplifier chips (not shown). To assemble the electrode array, the PDMS partition is aligned and pressed onto the backplate. Electrode solution is then introduced by first covering the chamber and applying vacuum, and then introducing solution into the upper compartment. Subsequent release of the vacuum allows the lower compartments to fill with solution. The excess solution in the upper compartment is then removed and replaced with bath solution.

Figure 11:
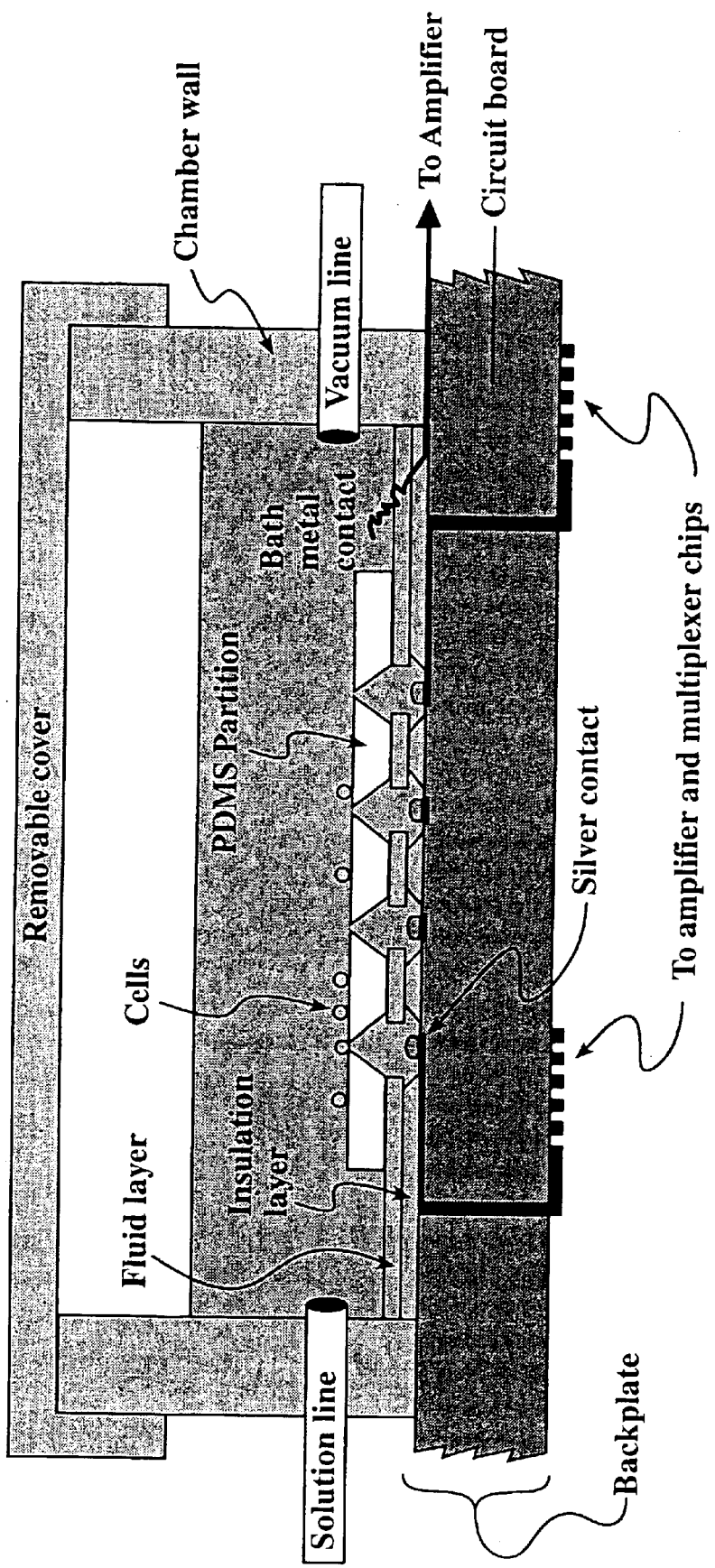

FIG. 11. PDMS patch electrode array system, including fluidic layer. This figure depicts an example of a PDMS patch electrode array with a fluidic layer. The electrode system is constructed from a backplate and a PDMS partition as in FIG. 10, but the backplate now includes an additional fluidic layer molded from PDMS. The fluidic channels are seen here in cross section, running normal to the plane of the page; they are continuous with individual electrode compartments to allow suction and/or fluid exchange without electrical contact between the compartments.

Figure 12:
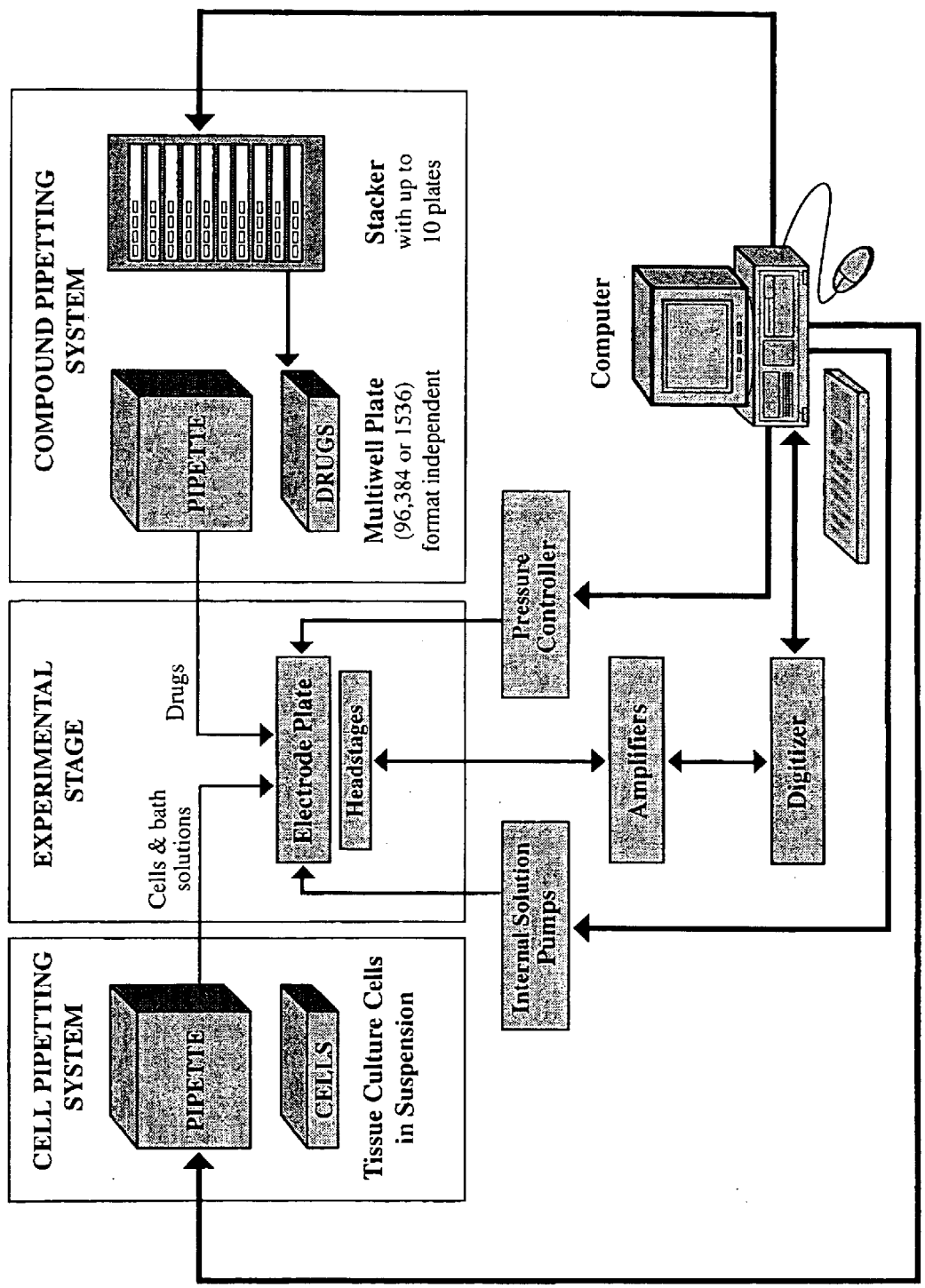

FIG. 12. This figure depicts a representative system incorporating the patch electrodes of the present invention.

DETAILED DESCRIPTION OF THE INVENTION

I. General Description.

The present invention relates to novel electrodes and associated fabrication methods for the patch clamp recording of membrane currents or voltages across/through biological membranes. In a preferred embodiment, the electrode partition is a micromolded sheet of silicone polymer whose surface adjoining an aperture has been oxidized to allow adherence to cell membranes.

The electrode partition, having a planar geometry, may be mounted on a backplate or backing that is also micromachined from appropriate materials such as silicon, quartz, glass or plastic to provide electrode compartments for the ionic solution and electrically conducting contacts (e.g., Ag—AgCl) for connection to an amplifier circuit. Additional supportive structures may be utilized as desired or required for use and handling.

In one embodiment of this invention, the electrode partition is disposable after a single use while the backplate and any associated supportive structures can be cleaned and reused with a new electrode partition. In an alternative embodiment, both the electrode partition and the backplate are both disposable after a single use. In this later instance, the supportive structure may or may not be disposed after a single use depending on whether the backplate is permanently attached to the supportive structure.

Optionally, microfluidic channels may be included in the partition structure for rapid exchange of the ionic solution. In particular, patch electrodes according to the present invention may be distinguished from the patch clamp electrodes of the prior art, in that the electrode partitions in the latter are individually prepared, typically from a glass capillary, to form a micropipette. By contrast, electrode partitions of the present invention have a planar geometry that permit direct integration into a planar microelectronic circuit as an array of patch electrodes, and can be mass produced using micromolding techniques for disposable use, and permit the making of a high resistance seal to a biological membrane by utilizing a chemically modified polymeric surface.

II. Definitions.

As used herein, the term "patch electrode" refers to a combination of the following components: 1) a partition, also called an electrode partition, that contains a small aperture that forms a high resistance seal (>100 Mohms) with a membrane and defines the collecting area of the electrode; and 2) a backplate containing an electrically conducting contact (e.g., a metal contact), such electrically conducting contact capable of being attached to an amplifier circuit. Associating the partition with the electrode results in the formation of a compartment, also called an electrode compartment, capable of containing an ionic solution.

As used herein, the term "bath solution" refers to the solution surrounding the cell. Usually, but not always, the bath solution is above the aperture, surrounding the cell. The specific bath solution used for measuring the ionic current through a biological membrane of a cell is usually chosen so that it is similar to the external ionic environment that the cell is exposed to in vivo. The bath solution in the planar electrodes of the present invention is analogous to the bath solution surrounding a glass pipette in a conventional glass electrode.

As used herein, the term "electrode solution", also referred to as "internal solution", refers to the solution sealed between the partition and the backplate. The specific electrode solution used for measuring the ionic current through a biological membrane of a cell is usually chosen so that it is similar to the intracellular solution of the cell. The bath solution and the electrode solution are typically chosen to be different when measuring the ionic current through a biological membrane of a cell; however, they may be the same for certain experimentally defined situations.

As used herein, the term "partition" refers to an insulating structure that separates a cell and its surrounding bath solution, on one side, from a compartment filled with electrode solution.

As used herein, the term "backplate" refers to a planar system that incorporates one or more electrically conductive contacts (e.g., metal contacts), wherein such electrically conducting contacts are capable of being connected to switching and/or amplifier circuits. The backplate is part of the patch electrode and caps-off the chamber when the backplate is in association with the chamber walls. In addition to the electrically conducting contacts of the patch electrode, the backplate may optionally incorporate one or more electrically conducting contacts for the bath solution (see, for example, FIG. 1). The switching and/or amplifier circuits may optionally be incorporated into the backplate. For example, the backplate may optionally comprise a single integrated chip, a multiple chip package or a hybrid of discrete electronic components and such chips. The patch clamp electrodes of the present invention may optionally further comprise fluidic channels and/or valves associated with the backplate. Preferably, the fluidic channels and/or valves used in the patch clamps of the present invention are microfluidic channels and/or microfluidic valves. In a preferred embodiment, the backplate comprises a layer which includes fluidic channels and/or valves (see, for example, FIGS. 3, 6 and 11). The fluidic channels and/or valves can be associated with the backplate using different methods known to those skilled in the art. For example, one or more fluidic channels and/or valves can be incorporated into a layer of the backplate. In a preferred embodiment using such methods, the fluidic channels and/or valves are molded into/as part of a PDMS layer of the backplate. In another example, the fluidic channels and/or valves can be fabricated into/on the backplate. In a preferred embodiment using such methods, the fluidic channels and/or valves are etched into/on a PDMS layer of the backplate.

As used herein, the term "supportive structure" refers to any material added to the patch electrodes of the present invention, wherein such material aids in the use and handling of the patch electrodes. One or more supportive structures may optionally be added at any desired location. The supportive structures may be composed of any suitable material.

As used herein, the term "aperture" refers to any opening, such as a hole, gap or slit. The opening can take any form, though it is usually elliptical, in particular circular or nearly circular. Apertures used in the present invention range in size from about 0.1 micron to about 100 microns. More preferably, the apertures used in the present invention range in size from about 1 micron to about 10 microns. Even more preferably, the apertures used in the present invention range in size from about 1 micron to about 2 microns.

As used herein, the term "chamber" refers to an area formed when chamber walls are associated with a backplate. FIGS. 1a, 5, 6, 10 and 11 depict an area formed when chamber walls are in association with backplates.

As used here, the term "compartment" refers to an area formed within the chamber. For example, the association of a partition and a backplate forms a compartment between the partition and the backplate (see, for example, FIG. 1).

As used herein, the term "amplifier" refers to a current-to-voltage converter and/or voltage-follower for recording small electrical signals. The voltage-follower allows accurate measuring of voltage signals.

As used herein, "electrically conductive contact" refers to an electrical connection between the solutions contained in the compartments and electronic circuits such as the voltage-clamp amplifiers. The electrically conductive contact can be a metal contact, such as a silver or platinum wire or pellet, a silver—silver chloride wire or pellet, or other non-polarizable material used by itself or in conjunction with a conductive liquid or gel, such as an agar gel formed in an ionic solution. In a preferred embodiment, the electrically conductive contact is a metal contact.

As used herein, the term "biological membrane" refers to a lipid bilayer surrounding a biological compartment such as a cell, including artificial cells, or a membrane vesicle or sheet.

As used herein, the term "polymer" refers to a polymeric or elastomeric material poured or injected into a mold as a liquid pre-polymer, cured to a solid state, and removed from the mold, retaining the shape of the master.

As used herein, the term "patch electrode array" refers to multiple patch electrodes arranged with fixed dimensions in a single well of a multi-well plate. In a preferred embodiment, the patch electrode array is organized in a format consistent with commercially available microtiter plates. In another preferred embodiment, the patch electrode array is organized in a format that can be used in any custom chamber designed/made by one skilled in the art.

As used herein, the term "electrode" refers to a physical connector that transmits or conducts electric signals.

As used herein, the term "FET" refers to a Field-Effect Transistor, or a transistor in which the resistance of the current path from source to drain is modulated by applying a transverse electric field between grid or gate electrodes; the electric field varies the thickness of the depletion layer between the gates, thereby reducing the conductance.

As used herein, the term "glass" refers to any of a large class of materials that are typically made by silicates fusing with, but not limited to, boric oxide, aluminum oxide, or phosphorous pentoxide.

Unless otherwise defined herein, as used herein, the term "high resistance seal" refers to a mechanically strong seal between cell membrane and electrode partition, whose integrity is shown by a high electrical resistance (typically 100 Mohms (100 MΩ) or greater) between the electrode compartment and the bath solution.

As used herein, the term "ion" refers to charged particles that result from the addition or removal of electrons from one or more atoms or molecules.

As used herein, the term "ionic" refers to of, containing, or involving an ion or ions.

As used herein, the phrase "ionic current" refers to the electric current resulting from the motion of ions.

As used herein, the term "microelectrode" refers to a patch electrode that is of appropriate size for recording signals from individual cells and is smaller than electrodes commonly used as, but not limited to, electric conductors in such things as electric cells, electric furnaces, thermionic tubes, gas-discharge devices, and semiconductor devices.

As used herein, the term "micron" designates a unit of length equal to one-thousandth ($10^{-3}$) of a millimeter or one-millionth ($10^{-6}$) of a meter. As used herein, the term micron is synonymous with each of the following: "micrometer", "$\mu$m" and "$\mu$".

As used herein, the term "micromachined" refers to fabricated by selective patterning of a substrate or a film atop a substrate to define shapes or structures. This may include methods of, but not limited to, microlithographic processing or standard machine-shop techniques.

As used herein, the term "micromolded" refers to an object having small features, as small as or smaller than micron scale, cast from a master mold that is micromachined or otherwise defined to have a small shape.

As used herein, the term "patch clamp" refers to a patch electrode configuration that allows the recording of signals from a biological membrane by placing a patch electrode in contact with a small area of the membrane.

As used herein, the term "whole-cell patch clamp" refers to a patch electrode configuration that allows the recording of signals from a cell by placing a patch electrode in contact with a small area of the cell.

As used herein, the term "PDMS" refers to silicone elastomer Poly-DiMethylSiloxane (poly-dimethylsiloxane), sometimes referred to as poly(demethyl siloxane). Commercially available sources of this material include, but are not limited to, PDMS-Sylgard Silicone Elastomer 1847 and Sylgard Curing Agent 184 (Dow Corning Corp., Midland, Mich.).

As used herein, the term "plastic" refers to materials formed from resins through the application of heat, pressure, or both. Examples of plastics include, but are not limited to, polyvinyl chloride, polyethylene, and urea-formaldehyde.

As used herein, the term "quartz" refers to a mineral composed of silica, chemical formula $SiO_2$.

As used herein, the term "silicon" refers to a group IV nonmetallic element, symbol Si, with atomic number 14.

As used herein, the term "silicone" refers to any group of semi-inorganic polymers of siloxane, characterized by high lubricity and thermal stability, extreme water repellence, and physiological inertness.

As used herein, the term "siloxane" refers to a family of silica-based polymers with the basic chemical structure, $R_2SiO$, wherein R is an alkyl group, usually methyl. Siloxanes can exist as, but not limited to, oily liquids, greases, rubbers, resins, or plastics. This term is synonymous with "oxosilane".

As used herein, the term "substrate" refers to a thin, planar material.

As used herein, the terms "chip" or "electronic chip" refer to a packaged electronic device.

As used herein, the term "patch clamp chip" refers to arrays of planar patch clamp electrodes of the present invention, wherein such arrays are capable of being used to measure ionic currents.

As used herein, the term "microfluidic valves" refers to isolation valves built into the electrode so that there is no fluidic, and therefore no electrical, connection between each electrode in an array.

As used herein, the term "cell membrane current" refers to the current measured across/through a biological membrane.

As used herein, the term "cell voltage" refers to the voltage measured across/through a biological membrane.

III. Specific Embodiments.

Prior to the present invention, the art had taught that patch clamp electrodes must be fabricated individually, and that the tips of glass micropipettes cannot be coated with other materials without impairing the ability to seal against biological membranes and record a meaningful current signal. In its most common form, the patch clamp technique suffers from several major disadvantages. First, establishing a recording requires a skilled operator who uses a micromanipulator to gently position the pipette tip onto a cell while viewing through a microscope. Thus, the use of patch clamp recording for large scale screening of expressed genes or drugs has been impractical due to its labor-intensive nature. Second, the resolution of the electrical recordings is affected by a substantial amount of noise in the detected signal. Such recordings are limited by instrumental noise sources, arising mainly from the large capacitance of the micropipette as compared to that of the small membrane patch. Third, the failure rate of patch clamp of the prior art is quite high, approaching 70 to 80 percent in some systems due mainly to the low probability of forming a high resistance seal. Lastly, exchange of the ionic solution is difficult, thus limiting the study of effects of pharmacological agents on the side of the membrane sealed to the partition.

The polymer partitions of the present invention and associated amplifier systems alleviate these foregoing disadvantages. A representative planar patch electrode of the present invention is depicted in FIG. 1b. The planar geometry eliminates the need for a skilled operator as a cell can be added to the bath solution over the partition and allowed to settle onto the aperture. In this case successful recording requires an adequate number of cells to ensure the likelihood of one cell landing on an aperture. An array of patch electrodes improves these odds as well as the success rate of obtaining a high resistance seal. The planar geometry also permits solution exchange on both sides of the electrode partition via microfluidic channels. Also, the small geometry and low dielectric constant of the partition material allow a lower electrical capacitance of the patch electrode to be realized, thereby improving the signal-to-noise ratio. In addition, the electrode partition can be made using fairly inexpensive, disposable materials.

The apparatuses and methods of the present invention may also be used for techniques such as, internal perfusion of oocytes, patch clamp electrophysiology, brain slice recording, receptor-ligand interactions on cell surfaces, calcium imaging studies, confocal microscopy, and in vivo microdialysis, for example. The system of the present invention may also be used to examine the function of ligand-gated ion channels, voltage-gated ion channels, G-protein coupled receptors, activities across the synapse, molecular transporters, cell-to-cell interactions and ion pumps.

A. Selection of Appropriate Polymeric Materials for the Partition.

Polymeric materials useful as cell interface materials are selected based on their ability to form a high resistance seal to a membrane. Any polymeric material that has exposed oxygen atoms at the surface or whose surface can be modified to mimic this behavior could be a candidate material for the patch partition of the present invention. Such polymeric materials may be identified by one skilled in the art using standard laboratory techniques based on the disclosures herein.

Preferably, the partition materials useful in the present invention include any polymeric materials which favor a high resistance seal, especially carbon-based polymers and silicon-based polymers. Even more preferably, the partition materials useful in the present invention is a silicone polymer poly-dimethylsiloxane (PDMS) surface that favors a high resistance seal when treated.

The preparation of silicone elastomers is well known to one skilled in the art. See, for example, U.S. Pat. Nos. 3,996,187 ("Optically Clear Filled Silicone Elastomers) and 6,013,715 ("Thermoplastic Silicone Elastomers"); Kleemann and Weber, *Elastomer Processing: Formulas and Tables*, Hanser Gardner Publications (1998); Cheremisinoff (Editor), *Elastomer Technology Handbook*, CRC Press (1993) and Donskoi, *Physico-Chemistry of Elastomer Heat-Shielding Materials*, Nova Science Publishers (1998), each of which is specifically incorporated by reference in its entirety.

PDMS is an example of a material that can be molded into an appropriate shape and whose surface can be modified to permit high resistance seal to a cell membrane. Thus, PDMS is one of the preferred polymeric materials to be used in the present invention.

B. Molding and Assembling the Patch Electrodes.

Appropriate methods for the molding and assembly of the planar patch clamp electrodes of the present invention are described in, for example, U.S. Pat. Nos. 4,427,614, 6,020,047 ("Polymer Films Having a Printed Self-Assembling Monolayer") and 6,014,259 ("Three Dimensional Imaging System"); *Science* 273:347 (Jul. 19, 1996), entitled "Complex Optical Surfaces Formed by Replica Molding Against Elastomeric Masters"; Parker, "Introduction to Injection Molding", In Modern Plastics Encyclopedia, pp. 264–268 (1989); Green, "Injection Molding Thermoplastics", Id, at 270–272.

For a discussion on general molding procedures to produce reliefs in elastomeric structures, including the fabrication of a molding master having a planar surface provided with a network of recessed channels, see, for example, E. Kim et al., *Nature* 376:581–584 (Aug. 17, 1995). Kim et al. disclose that PDMS is an elastomer which has a surface having a low interfacial free energy allowing it to maintain adhesion to various contacting surfaces. In this way, a PDMS surface can adhere to a curved surface. Furthermore, the authors note that PDMS molding structures have sufficient elasticity to allow its separation from the complementary relief structure to facilitate high-throughput manufacture of partitions.

An electrically conductive contact forms part of the backplate of the present invention as described elsewhere herein (see, for example, FIGS. 1*b* and 3).

The switching and/or amplifier circuits may also be incorporated into the backplate. For example, the backplate may comprise a single integrated circuit chip, a multiple-chip package or a hybrid of discrete electronic components and such chips. Methods of utilizing chips for detecting signals such as those employed by the present invention are well known in the art. See, for example, CRC Press (1998); Wolffenbuttel (Editor), *Silicon Sensors and Circuits: On-Chip Compatibility* (Sensor Physics and Technology Series, 3), Chapman & Hall (1996); Lau (Editor), *Chip on Board Technologies for Multichip Modules*, Kluwer Academic Publishers (1994); and Pecht, et al., *Guidebook for Managing Silicon Chip Reliability* (Electronic Packaging Series).

C. Chemical Modification of the Polymer Materials.

The surface of the polymeric material, such as PDMS, may be treated so as to modify its surface. For example, the surface of the polymeric material may be treated with an oxygen plasma or air plasma so as to modify its surface. Chemically, the free silicon atoms in the polymer combine with the oxygen atoms in the plasma to create $SiO_2$ at the surface, mimicking the surface of glass. See, for example, Younan Xia and George M. Whitesides, Soft Lithography, *Angew. Chem. Int. Ed.*, 37:550–575 (1998); and, David C. Duffy, J. Cooper McDonald, Oliver J. A. Schueller, and George M. Whitesides, Rapid Prototyping of Microfluidic Systems in Poly(dimethelsiloxane), *Analytical Chemistry*, 70(23), (1998).

D. Input of Cells and Solution into the Electrodes.

The addition of the cells and solution to the planar patch clamp electrodes of the present invention can be carried out in any one of a number of different ways. In the simplest embodiments, the cells and solution can be supplied directly into each container by any suitable method including but not limited to, pouring from above, immersing the electrodes in a solution, and by dispensing them using, for example, a pipette. The operation may be facilitated using any device capable of dispensing small amounts of liquid. Examples of such devices include, but are not limited to, ink jet printer heads, bubble printer heads and nQUAD aspirate dispensers. The cells and/or solution may be added through the open end of the container or through one or more openings in the cover.

In the case of planar patch clamp electrodes being completely enclosed, the container may be accessible through a system of channels, such as microfluidic channels or a microliquid handling system.

E. Microfluidic Channels and/or Valves.

As discussed immediately above, one or more fluidic channels and/or valves, preferably one or more microfluidic channels and/or valves (i.e., microliquid handling system), can be incorporated into the patch clamp electrodes of the present invention in order to permit fast solution exchange (i.e., perfusion) on both sides of the membrane being tested. Alternatively, the microfluidic channels and/or valves can be fabricated on the backing to be applied to the electrode partition, using normal etching techniques.

The solution can be held in a reservoir, usually a glass or plastic receptacle. Reservoirs are constructed so as to maintain a constant flow rate regardless of the level of solution in the reservoir. A constant flow rate may be important if the onset of response is influenced by agent application rate. Generally, each reservoir contains a glass or plastic siphon extending down through its cap into the solution and a vent line also extending into the solution that equilibrates chamber pressure for maintenance of constant flow rate. Solution-flow is by gravity feed and the flow rate can be controlled by adjusting the height of the reservoirs. Other methods of solution flow such as vacuum, pressure or pumping may also be used.

Dropwise removal of solution through the efflux line creates negative pressure in the chamber which is equilibrated by means of the vent line.

Solution flow between the reservoirs and the compartments is preferably controlled via miniature teflon-coated solenoid valves (Lee Valve Co.; Essex, Conn.). These valves are particularly suitable because of their corrosion resistance, biocompatibility and power requirements. Other valves exhibiting these characteristics may also be used. These
valves may be actuated by a direct current supplied from a direct current power source which would eliminate electrical hum. Direct current power sources may be, for example, a direct current power supply or a battery. The solenoid valves may be operated via computer controlled switching. For a complete description of the various options available for controlling the influx and efflux of the solution see, for example, U.S. Pat. No. 6,048,722, which is herein incorporated by reference in its entirety.

F. Ionic Solution.

The ionic solutions used in the bath solution and the electrode solution are selected to provide optimum readings for the particular cell under investigation. Usually the solutions are selected to optimize the flux through one channel type while reducing currents through others.

One skilled in the art selects the appropriate ionic solutions for the type of cell being measured and the experimental conditions of the measurement. Such ionic solutions are well known to those skilled in the art and include, but are not limited to, solutions which are generally based on potassium (K), sodium (Na) and calcium (Ca), all of which are usually buffered by HEPES. For example, to record potassium currents through oocytes, one might use (in mM): 150 KCl; 10 HEPES; 1 EGTA for the bath solution and 140 KCl; 1.8 $CaCl_2$; and 10 HEPES for the electrode solution.

For additional examples of suitable ionic solutions to use in the patch electrodes of the present invention, see, for example, the ionic solutions discussed in P. F. Baker, Intracellular Perfusion and Dialysis: Application to Large Nerve and Muscle Cells, In: Kostyuk et al. (editors), *Intracellular Perfusion of Excitable Cells*, John Wiley & Sons Ltd. (1984) Chapter 1, pages 10–13.

G. Amplification, Recording and Computer Equipment.

The conventional patch clamp amplifier circuitry used in the prior art is sufficient for use with the single planar patch clamp electrodes of the present invention. See, for example, Neher and Sakmann (Editors), *Single-Channel Recording*, Plenum Press (1995), and Nelson, *Operational Amplifier Circuits: Analysis and Design*, Butterworth-Heinemann (1995).

Examples of amplifiers useful with single planar patch clamp electrodes of the present invention include the HEKA Elektronik Single Electrode patch clamp amplifiers EPC-7, EC-8 and EPC-9; the Warner Instrument Corporation Patch Clamp amplifier PC-505A; Axon Instruments Capacitor-Feedback Patch Clamp amplifier Axopatch 200; and the Axon Instruments patch clamp amplifier MultiClamp 770A. An example of an appropriate multi-electrode patch clamp amplifiers useful with multiple electrodes of the present invention are the HEKA Elektronik Patch Clamp Amplifiers EPC9/2 and EPC9/3.

The voltage and current monitor output signals from a patch clamp amplifier are typically filtered by an analog filter, for example the Frequency Devices 902LPF filter, and digitized by analog-to-digital converters in a computer interface such as the Instrutech ITC-16, or the Axon Instruments Digidata 1322A. Such interfaces also provide digital-to-analog converters to provide stimulus voltages to the patch clamp amplifiers. The digitized signals are acquired and analyzed by software programs such as HEKA Electronik's Pulse program, or Axon Instruments' pCLAMP.

The automated system utilizing the planar patch clamp electrodes of the present invention can be readily adapted to patch clamp electrophysiology, calcium imaging studies, confocal microscopy and other applications where perfusion control and data acquisition need to be tightly integrated. Any type of biosensor capable of producing an electrical output, such as a sensor capable of measuring concentrations of substances within the cell, can be used in place of or in addition to the voltage-measuring electrode. Biosensors are well known to those of skill in the art and are reviewed for example by Lowe (Lowe, C. R. Biosensors, *Trends in Biotechnology,* 2:59–65, 1984) and by Byfield and Abuknesha (Byfield, M. P., Abuknesha, R. A. Biosensors & *Bioelectronics* 9:373–400 1994). Other automation aspects that may be optionally incorporated into systems utilizing the planar patch clamp electrodes of the present invention are digitally controlled voltage-clamp amplifiers and robotics and/or machine vision to automate the tasks of cell placement and microelectrode positioning to result in a fully automated electrophysiological assay system.

For a description of a current-to-voltage converter with low noise, wide bandwidth and high dynamic range that may be used with the patch electrodes of the present invention, see, for example, U.S. Pat. No. 5,237,493, assigned to International Business Machines Corporation (IBM), Armonk, N.Y.

The planar patch clamp electrodes of the present invention may optionally be linked in a system to any computer, computer workstation, dedicated processor, microprocessor or dedicated micro-controller.

H. Cell Placement on the Planar Clamp Electrode.

The planar patch electrodes of the present invention may optionally comprise means for receiving and automatically positioning a cell on the electrode partition immediately adjacent to the aperture. Positioning means may comprise indentations in the electrode partition for the cells to settle. Other positioning means well know to those skilled in the art include electrophoretic means, geometrical means such as the shaping of the container to facilitate cell positioning (e.g., using a funnel shape), the density and pattern of the electrodes in comparison with the test cells, suction means, robotic means, and artificial intelligence means for the proper positioning of the cells.

I. Cells Useful for Measuring Cell Membrane Currents.

The planar patch clamp electrodes of the present invention can be used to record from appropriate cells, including, but not limited to, cells of standard cultured mammalian cell lines.

In any cell, the existence of a membrane potential is dependent on the presence of a gradient of ions. Ion gradients are essential in driving various biological processes. For example, the transmembrane concentration gradients of sodium and potassium ions are essential for conductance of electrical impulse down the axon of a nerve cell. In many cells, the increase in the concentration of calcium ion is an important regulatory signal. In muscle cells, an increase in calcium concentration initiates contraction, and in exocrine cells of the pancreas, it triggers secretion of digestive enzymes.

Cell lines and cells which have been used for measuring cell membrane currents are well known to those skilled in the art and include, but are not limited to those of bacterial, yeast, insect, and mammalian origin. For example, Bacillus spp., *Escherichia coli,* Streptococcus spp., Streptomyces spp., Pseudomonas spp. and other lower eukaryotic cells will find use with the present planar patch clamp electrodes. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica.*

A number of mammalian cell lines useful for measuring cell membrane currents are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells NIH/3T3, 293 cells (ATCC #CRL 1573),COS-7, 293, BHK, CHO, TM4, CV1, VERO-76, HELA, MDCK, BRL 3A, W138, Hep G2, MMT 060562, TRI cells, as well as others. A well known example of an avian cell line is the chicken B cell line "DT-40". Examples of vectors useful for transforming such cell lines include, but are not limited to, retroviral vectors, vaccinia virus vectors, adenovirus vectors, herpes virus vector, fowl pox virus vector, bacterial expression vectors, plasmids, such as pcDNA3 (Invitrogen, San Diego, Calif.) or the baculovirus transfer vectors.

Insect cell lines may also be used with the planar patch electrodes of the present invention. Insect cells for use with baculovirus expression vectors include, inter alia, *Aedes aegypti, Autographa californica, Bombyx mori, Drosophila melanogaster, Spodoptera frugiperda,* and *Trichoplusia ni.* Drosophila cells may be transfected with commonly available vectors (G. M. Rubin et al., *Nucl. Acids Res.* 11:6341–6351 (1983); G. M. Rubin et al., *Science* 218:348 (1982)).

Specific animal cells suitable for measuring ionic currents using the patch electrodes of the present invention include, but are not limited to, leukemia L1210 cells (In Modern Pharmacology, pp. 1121–1129 (1978)); guinea pig heart cells (Journal of Physiology 397:237–258 (1988); starfish egg cells (The Journal of General Physiology 70:269–281 (1977) and denervated frog muscle fibers (Neher et al., *Nature* 260 (Apr. 29, 1976).

As another example, inhibition of isolated specific ionic currents within individual dorsal root ganglion or spinal dorsal horn neurons can be measured using the planar patch clamp electrodes of the present invention. In addition, the change in ionic currents can be measured after exposing these cells to analgesic peptides from the venom of *Grammostola spatulata*. See, for example, U.S. Pat. Nos. 5,877,026 and 5,807,821 ("Analgesic Peptides from Venom of *Grammostola spatulata* and Use Thereof").

The planar patch clamp electrodes of the present invention may also be used to measure the ionic current in specially transformed cells, such as cells expressing inward rectifier potassium channel cDNAs (U.S. Pat. No. 5,670,335). Alternatively, cells can be contacted with compositions to see if they alter the rate or type of ionic current across the cellular membrane. For example, contacting nerve cells with pregnenolone sulfate results in a 3-fold increase in the ionic current across the cellular membrane (U.S. Pat. No. 5,366,968).

The electrodes of the present invention can also be used to measure the ionic current of artificial membranes, especially those with incorporated ion channels. For information on the production and uses of artificial cells, see, for example, Christopher Miller, Ion Channel Reconstitution, *Plenum*, 577 (1986) and U.S. Pat. Nos. 6,143,501, 5,932,459, 5,858,746, 6,103,217 and 6,109,852.

J. Electrophysiological Analysis of Transfected Cells Expressing Recombinant Proteins.

The use of patch clamp for electrophysiological analysis of transfected cells expressing recombinant proteins is well known to the skilled artisan. Electrophysiological measurements are useful for assessing the activity of recombinant proteins in response to agonists and antagonists. Electrophysiological studies have been used to characterize cloned ion channels, transporters, receptors, and various other membrane-bound proteins expressed by host cells transformed or transfected with their encoding nucleic acids. Host cells and vectors for transformation or transfection are discussed in the previous section.

Since insect cells are relatively easy to patch clamp and uninfected cells are electrophysiologically quiet, transfected insects cells have been used in electrophysiological studies employing patch clamp techniques to detect the functions of the expressed protein. Klaiber et al. conducted electrophysiological studies on insect cells expressing the Shaker channel (Klaiber et al., *Neuron*, 5, 221, (1990)). Kartner et al. teaches insect cells expressing the cystic fibrosis gene product CFTR for electrophysiological studies (Kartner et al., *Cell*, 64, 681, (1991)). Cascio et al. discloses insect cells expressing homomeric α glycine receptors for similar studies (Cascio et al., *J.Biol. Chem.* 268, 22135 (1993)).

Electrophysiological studies have also been performed using Xenopus oocytes transfected with nucleic acid encoding recombinant protein. U.S. Pat. No. 5,827,655 teaches the use of patch clamp techniques in the electrophysiological study of a murine potassium channel expressed in Xenopus oocytes. U.S. Pat. No. 6,020,143 discloses the use of patch clamp to determine presenilin-related or presenilin-mediated ion channel activity using Xenopus oocytes or HEK293 cells transfected with the nucleic acid encoding presenilin. Presenilin is a membrane associated protein expected to interact with ion receptors or channels. U.S. Pat. No. 5,985,603 discloses the use of Xenopus oocyte expressing $P_{2X}$ purinoreceptor, a ligand-gated ion channel, for determining the functional activity of the purinoreceptor to its ligand ATP.

Moreover, electrophysiological studies have been performed using membrane preparations of transfected host cells expressing the desired protein. U.S. Pat. No. 5,552,308 teaches the use of patch clamp to measure serotonin transporter activity using membrane preparations from cells transfected with the nucleic acid encoding the transporter.

Further, U.S. patents disclose electrophysiological studies performed with artificial lipid membranes. Any of the recombinantly made proteins discussed above can be inserted into an artificial membrane system for functional studies. U.S. Pat. No. 5,795,782 teaches the use of patch clamp techniques for studying artificial bilayer reconstituted with a purified pore protein. U.S. Pat. No. 6,022,720 discloses pro-apoptotic protein Bax inserts into lipid membranes and forms channels. The patent also discloses planar lipid bilayers containing Bax for measurement of Bax activity using patch clamp techniques.

The patch electrodes of the present invention may be used in electrophysiological studies for determining the activity of receptors, transporters, and ion channels.

K. Electrophysiological Analysis of Cells Injected With Various Agents.

The planar patch clamp electrodes of the present invention may comprise optional means of injecting one or more injection solutions into said oocyte between the culturing and measuring step. The injection solution may comprise an agent. The agent may be a chemical, a
protein or a nucleic acid.

Examples of agents that may be injected include proteins, DNA, RNA, PNA, receptor agonists, receptor antagonists, neurotransmitter, neurotransmitter analogues, enzyme inhibitors, ion channel modulators, G-protein coupled receptor modulators, transport inhibitors, hormones, peptides, toxins, antibodies, pharmaceutical agents, chemicals and combinations of these agents. Specific agents which are of interest include purinergics, cholinergics, serotonergics, dopaminergics, anesthetics, benzodiazepines, barbiturates, steroids, alcohols, metal cations, cannabinoids, cholecystokinins, cytokines, excitatory amino acids, GABAergics, gangliosides, histaminergics, melatonins, neuropeptides, neurotoxins, endothelins, NO compounds, opioids, sigma receptor ligands, somatostatins, tachykinins, angiotensins, bombesins, bradykinins, prostaglandins and combinations of these agents.

L. Arrays.

Multiple patch electrodes can be fabricated into the same device as an array. Thus, the planar patch clamp electrodes of the present invention can be utilized to produce highly-parallel electrode arrays which enable multiple, simultaneous, single-cell electrical recordings (or multiple site recordings from a large single cell). Both single-channel and whole-cell currents can be measured with high fidelity using the arrays of the present invention. The high parallelism provided by the present invention increases the throughput of patch clamp screening by several orders of magnitude, enabling industrial-scale screening of pharmaceutical agents. Thus, this invention makes it possible to produce patch clamp electrodes capable of measuring thousands of mammalian cells in parallel.

Patch clamp chip technology requires sophisticated electronic circuit that includes multiple amplifiers and a switching circuit. Computer control of the circuit is also necessary to do the switching and testing. The use of microcomputers in measuring biological signaling is known to one of skill in the art. See, for example, Neher and Sakmann (Editors), *Single-Channel Recording*, Plenum Press (1995), O'Neill and Fillenz, Microcomputer-Controlled Voltammetry in the Analysis of Transmitter Release in Rat Brain, *Ann. N.Y. Acad. Sci.* 473:337–3348 (1986); Sigworth, *Design of the EPC-9, a computer-controlled patch-clamp amplifier. 1. Hardware*, J. Neurosci. Methods 56:195–202(1995); Sigworth et al., *Design of the EPC-9, a computer-controlled patch-clamp amplifier. 2. Software*, J. Neurosci. Methods 56:203–215 (1995).

M. High-throughput Screening.

Ion channel activity is important for studying many medical disorders, among them migraine headaches, epilepsy, irregular heartbeat and cystic fibrosis.

A search for genes encoding ion channels or transporter proteins could be carried out by parallel transfection of cells with genes to be tested, followed by screening for ionic currents in a high-throughput screening device as described herein.

The planar patch clamp electrodes of the present invention have applications in the area of high-throughput screening in order to determine the effects of various types of compounds on cells. For example, the patch electrodes disclosed herein can be used to screen for the effects of various pharmacological agents, environmental pollutants, toxins and poisons on cell membrane currents. High-throughput screening using the planar patch clamp electrodes of the present invention can also be used to identify and help design drugs which act on cell-membrane ion channels and transporters.

The system may also be useful for screening compound libraries to search for novel classes of compounds, screening members of a given class of compounds for effects on specific receptors, detailed pharmacological characterizations of compounds having receptor effects, rapid evaluation of $EC_{50}$ (potency) and $E_{max}$ (efficiency), investigation of interactions between receptors and rapid characterization of a series of receptor mutants. The invention provides repetitive application, dose-response data generation, evaluation of receptors expressed from poly $A^{+mRNA}$, and evaluation of recombinant receptors such as, for example, γ-aminobutyricacid (GABA) receptors, kainate receptors, and N-Methyl-D-aspartic acid (NMDA) receptors.

Examples of agents that may be used for the apparatus and methods of the invention include drugs, receptor agonists, receptor antagonists, neurotransmitter, neurotransmitter analogues, enzyme inhibitors, ion channel modulators, G-protein coupled receptor modulators, transport inhibitors, hormones, peptides, toxins, antibodies, pharmaceutical agents, chemicals and combinations of these agents. Specific agents which may be used for the apparatus and methods of the invention include purinergics, cholinergics, serotonergics, dopaminergics, anesthetics, benzodiazepines, barbiturates, steroids, alcohols, metal cations, cannabinoids, cholecystokinins, cytokines, excitatory amino acids, GABAergics, gangliosides, histaminergics, melatonins, neuropeptides, neurotoxins, endothelins, NO compounds, opioids, sigma receptor ligands, somatostatins, tachykinins, angiotensins, bombesins, bradykinins, prostaglandins and combinations of these agents.

A representative system for high-throughput screening which utilizes the patch clamp electrodes of the present invention is provided in FIG. 12.

For general information on high-throughput screening, see, for example, *Cost-Effective Strategies for Automated and Accelerated High-Throughput Screening*, IBCS Biomedical Library Series, IBC United States Conferences (February, 1996); John P. Devlin (Editor), *High Throughput Screening*, Marcel Kedder (1998); and U.S. Pat. Nos. 5,763, 263, 5,837,508 and 6,008,203.

EXAMPLES

The following examples are provided to describe and illustrate the present invention. As such, they should not be construed to limit the scope of the invention. Those in the art will well appreciate that many other embodiments also fall within the scope of the invention, as it is described hereinabove and in the claims.

Example 1

Assembly of Polymer Patch Clamp Electrode

Suitable polymeric materials for constructing the electrode partitions of the present invention are provided in Specific Embodiments, Section III.A., above. PDMS is the preferred polymeric material to use for making the planar patch clamp electrode partitions as described in this example. PDMS-Sylgard Silicone Elastomer 184 and Sylgard Curing Agent 184 are available commercially from Dow Corning Corp., Midland, Mich.

The patch electrode assembly is composed of two major parts, the partition and the backplate (FIGS. 1 and 3).

The first is a micromolded polymeric partition with one or more small apertures, each aperture on the order of from about 0.1 microns to about 100 microns in diameter. In various preferred embodiments, the aperture size depends upon the requirements of the particular measurement being collected. Thus, in various preferred embodiments, the aperture size ranges from about 0.1 microns to about 1 micron; from about 1 micron to about 2 microns; from about 1 micron to about 5 microns; from about 1 micron to about 10 microns; from about 10 microns to about 20 microns; from about 20 microns to about 50 microns; and from about 50 microns to about 100 microns. In a preferred embodiment, the aperture is about 1 micron to about 10 microns in size. In another preferred embodiment, the aperture is about 1 micron to about 2 microns in diameter.

Figure 2:
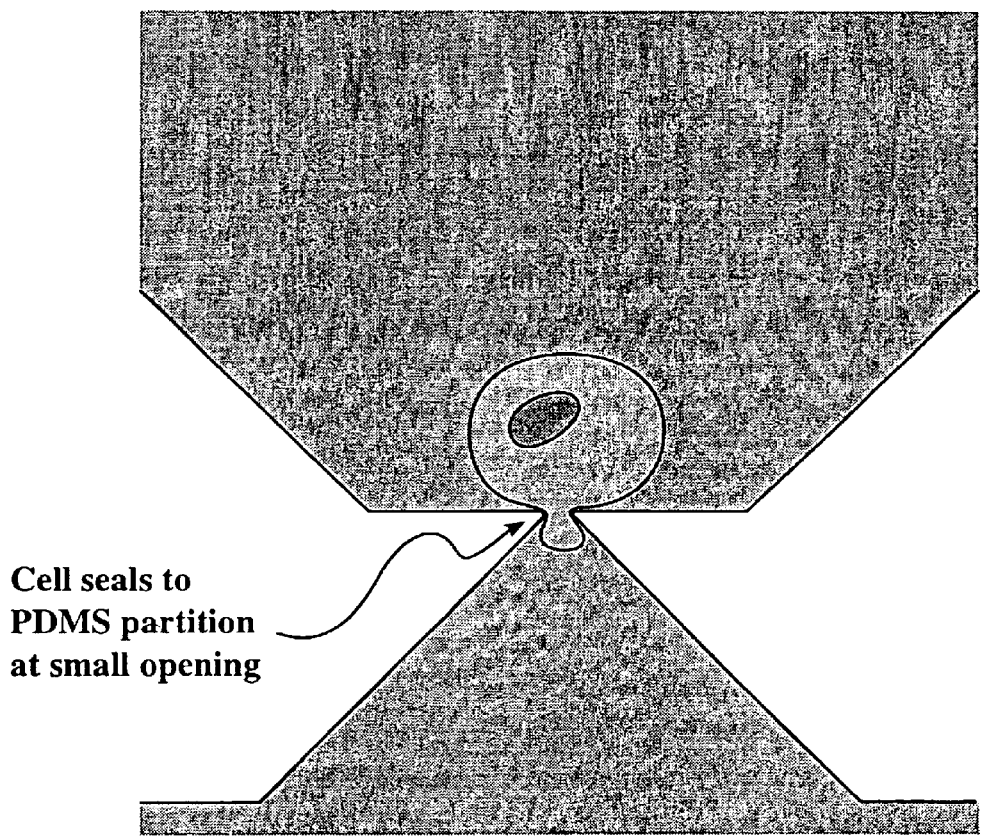
FIG. 2. Close-up of cell contact point to partition. This figure illustrates the points of contact between the aperture of a partition according to the present invention and a test cell.

The top surface of the partition is preferably shaped so as to improve the chances of cell adhesion over the aperture (see, for example, FIG. 2).

The bottom surface of the partition is preferably molded to define the top and side walls of the electrode chamber, and may incorporate channels and flaps or other structures that define pathways and valves for ionic solution exchange, if desired. Valves provide electrical isolation between individual electrode chambers when recordings are being made.

The polymeric partition should be modified in such a way as is mentioned in Section III.C., above, so as to permit a high resistance seal to a biological membrane.

The second part of the patch electrode assembly is a backplate that also forms the bottom wall of the electrode chamber (FIGS. 1 and 3). This part also contains one or more electrically conducting contacts (e.g., metal contacts), typically silver with a surface layer converted to AgCl and, optionally, the switching and amplifier circuitry. It may further include additional electrically conducting contacts that communicate directly with the bath solution through large apertures in the partition—these contacts comprise the "reference" or "bath" electrodes. To allow precise assembly of the partition and the backplate, a pattern of etched pits or trenches in the backplate receives dimples molded into the partition to enforce alignment of the structures (FIGS. 5 and 6).

The microfluidic channels may be included in the molded polymeric structure or as a second polymeric sheet that is sandwiched between the cell interface sheet and the backplate. Alternatively, the channels may also be etched into the backplate.

Preferably, common solution inlet and outlet lines are provided for all of the patch electrodes that in turn can be connected to a larger reservoir of solution that can be controlled by standard fluidic couplers. To avoid electrical crosstalk among the patch electrodes, microfluidic isolation is required at each patch electrode.

To assemble the patch electrode, the polymeric sheet is pressed onto the backplate, including any supportive structures, to form a temporary seal that electrically and fluidically isolates the patch electrode from the surroundings. Preferably, this assembling process may be done in a bath of the ionic solution to fill the electrode chamber and to minimize air bubbles.

The procedures for the molding and assembly of the patch electrodes of the present invention are well known to one skilled in the art, as set forth in Specific Embodiments, Section III.B., above.

Example 2

Chemical Treatment of Polymeric Electrode Partitions

In a preferred treatment of the polymeric patch electrode partitions prepared in Example 1, the polymeric material is exposed to a high-voltage discharge for 10 minutes in an atmosphere of 1 millitorr of air. This treatment provides suitable modification of the partitions of the present invention so that a high resistance seal to a biological membrane can be achieved.

The effectiveness of this treatment may be tested by comparing the hydrophobicity before and after treatment. This is done by applying a drop of water to the surface. Before treatment the surface should be hydrophobic and so that the drop of water balls up. After treatment the surface should be hydrophilic so that the drop of water flattens across the surface with a very small contact angle.

Example 3

Attaching the Patch Electrodes to Suitable Amplification and Recording Equipment So as to allow recordings from a large array of patch electrodes, an integrated circuit is preferred to provide simple integration of electrode and amplifier functions. Because the backplate forms part of the patch electrode chamber of the present invention and is exposed to the ionic solution, the backplate surface preferably has a thick passivation layer to reduce capacitance and protect underlying circuitry. Most preferably, only the silver contact metallizations protrude through this passivation layer.

A pair of FET switches allow each silver contact to be connected either to a reference voltage or to the input of an amplifier (FIGS. 1 and 7). The amplifier circuit is designed to detect currents in the picoampere to nanoampere range. This may be accomplished through the use of a low-noise operational amplifier and an appropriate feedback impedance, either a large resistance (e.g., 1 giga-ohm) or a small capacitance (e.g., 1 pF) with an associated FET discharge switch.

Thus, the assembled planar patch clamp electrodes of Examples 1 and 2 can be hooked up to conventional patch clamp amplifier circuitry, wherein such circuitry is sufficient for use with a single patch clamp electrode or an array of patch clamp electrodes. Examples of suitable amplification and recording equipment is provided in the Specific Embodiments, Section III.G., above.

Optionally integrated on the backplate may be subsequent signal conditioning means, for example a differentiator (in the case of capacitor feedback), voltage amplification, filtering, series-resistance compensation and/or analog-to-digital conversion.

Example 4

Measuring Individual Cell Membrane Currents

Individual cells may be added to the bath and allowed to settle onto the patch electrode array at the bottom of the well. Individual patch electrodes are then tested sequentially by using the switching circuit to connect each one to the amplifier.

The membrane current change is measured for a given (e.g., 10 mV) reference voltage change in order to calculate seal resistance. An electrode showing a sufficiently high resistance is then selected for patch recording.

For whole-cell recording the biological membrane spanning the aperture is first ruptured to provide access to the cell interior. A common way to do this is to apply a brief, biphasic high voltage pulse (500 to 800 mV) and/or suction underneath the aperture.

Example 5

Measuring Multisite Cell Membrane Currents

Multisite recordings from a cell population is possible if many cells are sealed to multiple patch electrodes in the array (FIGS. 4, 7, 10 and 11).

A population of cells is placed onto the patch electrode array and each patch electrode tested via the switching circuit for sufficiently high resistance seals. A common stimulus voltage pattern may be applied to the reference input of each amplifier or, alternatively, individual patterns could be applied. The resulting membrane current recordings are acquired simultaneously.

Example 6

Measuring the Activity of Ion Channels

Ion channel activity is measured as the current recorded through the membrane sealed to the partition. Typically, the patch electrode controls the membrane potential and the current is recorded as that necessary to maintain the voltage.

Example 7

High-throughput Screening

The patch electrode arrays may be fashioned into a standard 96 or 384 well microtiter plate for the application of cells and pharmacological agents (FIGS. 4, 5, 6, 7, 10 and 11).

The effects of various agents on the membrane current activity is recorded as an electrical response. Each well can assay a different pharmacological agent thereby increasing the throughput of the screening. Screening would typically make use of whole-cell recordings of current or, alternatively, membrane potential. The latter would make use of an amplifier with additional circuitry to allow "current clamp" (i.e., voltage-follower circuitry).

Example 8

Recording of Currents of the Shaker Potassium Channel from Xenopus oocytes

To further demonstrate various aspects of this invention, we prepared a single planar patch clamp electrode that we have used for testing purposes.

In summary, the strategy we employed was to mimic the shape and size of the tip of the standard glass micropipette by casting a PDMS mold directly from a quartz rod pulled to a small tapered point, as described in the Background of the Invention. After the polymer cured, the quartz rod was carefully removed from the PDMS, leaving a block of polymer with a hollow cavity at its center in the shape of the quartz rod. The block of PDMS was then sliced perpendicular to the cavity as thin sheets (200 microns thick). Once the slicing reached the hollow cavity, a small hole appeared in the PDMS sheet. The size of the aperture (about 0.1 micron to about 100 microns) matched the size of the tip of the quartz rod with a tapered shape. The PDMS sheet can be used as the cell interface for the planar patch electrode.

To assemble the patch electrode, the PDMS sheet was glued to its support structure, a plastic coverslip. Care was taken to align the small hole in the PDMS sheet to a 1 millimeter hole drilled in the center of the coverslip. The mounted PDMS sheet was then exposed to a 10 minute glow discharge to chemically modify the surface properties, thus oxidizing the surface. Next, the mounted PDMS sheet was sandwiched between a standard bath compartment above and an electrode compartment below. The electrode compartment comprises a small volume of ionic solution, a chlorided silver wire, and PE tubing for solution flow. The entire assembly was placed onto the stage of an inverted microscope and the silver wire was connected to the headstage input of the Axopatch 200B amplifier. The bath compartment was filled with bath solution and then connected to the ground of the amplifier via another Ag—AgCl wire.

To make a patch recording, a Xenopus oocyte was dropped onto the small aperture after removing the vitelline membrane. After 5 minutes, the membrane formed a high resistance seal to the patch electrode so that ionic currents could be recorded from the patch of membrane sealed to the electrode partition. If the membrane did not seal to the partition within a few minutes, then a slight suction was applied through the solution lines from the electrode compartment side to facilitate seal formation. The specific steps are as follows:

Molding. We suspended a quartz rod vertically into a 30 ml beaker that was ¾ full of water. The tip of the rod just touched the surface of the water. The freshly mixed PDMS was then poured to fill the beaker.

The PDMS floated on top of the water and formed an exaggerated meniscus at the water interface to fully surround the tip of the quartz rod while an inch or so of the other end of the quartz rod remained uncovered above the PDMS.

The resultant assembly was then left to cure, either at room temperature overnight or at 65° C. for at least 4 hours. Once the PDMS cured it formed a strong seal (though not permanent) to the glass walls of the beaker so that the quartz rod could be removed intact by carefully pulling it out of the PDMS.

Next, the PDMS was removed from the beaker using a sharp instrument such as forceps so as to pry the PDMS away from the glass walls of the beaker.

Slicing. We used a standard laboratory microtome to slice the PDMS block. First, the PDMS block was mounted on the movable stage using silicone adhesive. The stage was raised so that the razor blade of the microtome just met the top of the PDMS block. The speed of advancement and vibrational speed of the blade were adjusted to minimize movement of the PDMS block as the blade cut through it. The thickness of the cut was adjusted to 200 microns. As the sectioning got closer to the hollow cavity, a small circle around the location of the hole was marked on the top of each sheet. This process made it easier to find the hole under the microscope when mounting the PDMS sheet to the plastic coverslip.

Mounting. The PDMS sheet was glued to the plastic coverslip with silicone adhesive and left to dry overnight. As the aperture was on the order of a few microns, it had to be located with a high magnification microscope. Then the plastic coverslip could be coated with the silicone adhesive and carefully positioned onto the PDMS sheet with the large hole of the plastic coverslip circling the small hole in the PDMS sheet.

Attaching the Patch Electrode to Suitable Amplification Equipment. Next, the silver wire in the bottom compartment was connected to the headstage input of the Axopatch 200B amplifier and the cell current measurements were recorded.

Measuring the Cell Membrane Current of the Xenopus Oocyte. The recorded currents are provided in FIG. 8 and the description accompanying FIG. 8, above.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Example 9

Planar Patch Clamp Electrode Arrays

We describe here the fabrication of planar patch clamp electrode arrays with and without fluidic channels. In both cases an array consists of a micromolded PDMS partition sealed to a circuit board containing electrically conductive contacts (e.g., the metal contacts shown in FIGS. 10 and 11). In overview, the PDMS partition is fabricated through a series of micromolding steps beginning with a master structure micromachined into a silicon substrate (hereafter called the Si master). From the Si master which contains pyramidal pits a series of three molding steps (described below) results in a polyurethane (PU) structure containing raised pyramids. This PU structure will form the bottom, and a glass slide the top, of the mold for the final PDMS partition.

More explicitly, here are the steps in the fabrication of a PDMS partition, as illustrated in FIG. 9. First, the Si master structure is created. A 4-inch silicon wafer is etched by exposure to KOH using standard photolithography and micromachining techniques (Madou, M. 1997. *Fundamental of Microfabrication*, CRC Press LLC) to produce self-terminated, pyramidal pits. The pits are 16×16 arrays on 1 millimeter or 2 millimeter centers, and are 400 microns deep. PDMS resin is poured over the Si master and cured in an oven at 60 degrees C. The cured PDMS contains pyramids mirroring the pyramidal pits of the Si master. (PDMS, rather than the more rigid polyurethane (PU) is used at this step because its elasticity allows easy separation from the Si master.) This PDMS sheet is then treated to an oxygen plasma (10 minute glow discharge) to oxidize the surface.

Fresh PDMS is then poured onto the oxidized PDMS and allowed to cure. The two PDMS sheets are separated (this is made possible by the surface treatment of the first PDMS mold). The second-generation PDMS sheet contains pyramidal pits, identical to the original Si master.

In the third molding step, polyurethane resin is poured over the second generation PDMS sheet and cured by exposure to ultraviolet light to form a structure with raised pyramids (hereafter called the PU mold).

In the final molding step, PDMS resin is poured onto the PU mold, with a glass slide defining the top surface. The areas of contact between the tips of the PU pyramids and the glass slide define the electrode apertures in the electrode array. Once the PDMS is cured, the mold is released to reveal the planar PDMS partition.

The back plate for the patch clamp electrode array is a double-sided fiberglass-epoxy circuit board patterned to have an array of 16 contacts, matching the array of holes in the partition. The copper conductors on the circuit board are coated with silver paint to form the silver electrode contacts. A thin (0.2 millimeter to 0.4 millimeter) insulating layer of PDMS is cured on the surface of the circuit board; a hole is cut in this layer at each electrically conducting contact. The insulating layer seals well against the PDMS partition, ensuring electrical isolation of the individual electrodes. The insulating layer also anchors a silver wire that acts as the bath electrode. The silver contacts and silver wire are treated with bleach (Clorox®) to produce a silver-chloride (AgCl) coating.

In addition to the insulating layer, an additional PDMS layer containing fluidic channels is optionally placed over the back plate as shown in FIG. 11. These channels allow suction to be applied to the electrodes while maintaining electrical isolation. The application of suction generally aids the formation of high-resistance seals to cell membranes.

The PDMS partition is manually aligned with the back plate and pressed onto it. Filling the electrode chambers with solution is then performed as follows. First, an airtight cover is placed over the top chamber and vacuum is applied to the top chamber. Without releasing the vacuum, electrode solution is then introduced into the top chamber, partially filling the top chamber. The vacuum in the top chamber is then released so that vacuum in the electrode chambers pulls the solution into the chambers, filling them completely. The top cover is removed, and the fluid in the top chamber is manually exchanged for the appropriate bath solution.

The electrically conducting contacts on the circuit board connect via through-holes to electronic chips mounted on the backside of the board. A multiplexer chip (MAX 336) performs the switching function, connecting one of 16 contacts to the input of the amplifier. An operational amplifier (AD 548) with a 20 megohm feedback resistor serves as the current-to-voltage converter. The output signal from the board is fed to a filter and analog-to-digital converter for processing by computer.

To make patch clamp recordings using this system, a suspension of isolated cells in saline solution is added to the bath compartment. After a few minutes the cells settle onto the partition. Membrane currents may then be recorded from any cell that lands onto an aperture in the PDMS partition and forms a high resistance seal.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

ADDITIONAL REFERENCES

I. Patch Clamp

Hamill, O. P., A. Marty, E. Neher, B. Sakmann, and F. J. Sigworth, Improved patch-clamp techniques for high-resolution current recording from cells and cell-free membrane patches, *Pflugers Arch.* 391:85–100 (1981).

Sigworth, F. J., The patch clamp is more useful than anyone had expected, *Fed Proc* 45 (12):2673–2677 (1986).

Levis, R. A. and J. L. Rae, The use of quartz patch pipettes for low noise single channel recording, *Biophy. J.* 65:1666–1677 (1993).

II. Microfabrication of Quartz

Danel, J. S., F. Michel, and G. Delapierre, Micromachining of quartz and its application to an acceleration sensor, *Sensors and Actuators.* A21–23:971–977 (1990).

Hedlund, C., U. Lindberg, U. Bucht, and J. Soderkvist, Anisotropic etching of Z-cut quartz, *J. Micromech. Microeng.* 3:65–73 (1993).

Rangsten, P., C. Hedlund, I. V. Katardjiev, and Y. Backlund, Etch rates of crystallographic planes in Z-cut quartz-experiments and simulation, *J. Micromech. Microeng.* 8:1–6 (1998).

III. PDMS Molding

Information about Electrical/Electronic Materials, *Dow Corning Bulletin* 67–005, Date 4/70.

Silicones for electronic design, *Dow Corning Bulletin* 01–236, Date 11/72.

What is claimed is:

1. An electrode comprising:
   a). a silicone polymer molded so as to form a partition comprising an aperture, said apertured-partition capable of forming a high resistance seal of at least 100 MΩ with a biological membrane; and
   b). a backplate associated with the apertured-partition, said backplate comprising an electrically conductive contact, wherein the association of the apertured-partition and the backplate forms a compartment associated with the aperture, and wherein the said compartment contains the electrically conductive contact.

2. The electrode of claim 1 further comprising walls associated with the electrode so as to form a chamber.

3. An apparatus for measuring ionic currents through a biological membrane, said apparatus comprising:
   a). an electrode comprising:
      i). a silicone polymer molded so as to form a partition comprising an aperture, said apertured-partition capable of forming a high resistance seal of at least 100 MΩ with a biological membrane; and
      ii). a backplate associated with the apertured-partition, said backplate comprising an electrically conductive contact, wherein the association of the apertured-partition and the backplate forms a first compartment associated with the aperture, and wherein the said first compartment contains the electrically conductive contact and a first solution; and
   b). walls associated with the electrode so as to form a chamber, said chamber comprising a second compartment containing a second solution.

4. The apparatus of claim 3, wherein the first and second solution is the same.

5. The apparatus of claim 3, wherein the first and second solution is different.

6. The electrode of claim 1 or claim 3 wherein the surface of the silicone polymer adjoining the aperture has been oxidized.

7. The electrode of claim 1 or claim 3 wherein the size of the aperture is from about 0.1 micron to about 100 microns.

8. The electrode of claim 1 or claim 3 wherein the size of the aperture is from about 1 micron to about 20 microns.

9. The electrode of claim 1 or claim 3 wherein the size of the aperture is from about 1 micron to about 10 microns.

10. The electrode of claim 1 or claim 3 wherein the size of the aperture is from about 1 micron to about 2 microns.

11. The electrode of claim 1 or claim 3 wherein the silicone polymer is poly-dimethylsiloxane.

12. The apparatus of claim 3 further comprising a switching circuit associated with the electrically conductive contact.

13. The apparatus of claim 3 further comprising an amplifier associated with the electrically conductive contact.

14. The apparatus of claim 12 or claim 13 further comprising a recording means.

15. The apparatus of claim 14 wherein the recording means is selected from the group consisting of a digital recorder, a computer, volatile memory, involatile memory, chart recorder, and combinations thereof.

16. The electrode of claim 1 or claim 3 further comprising one or more supportive structures associated with the partition.

17. The electrode of claim 1 or claim 3 further comprising a microfluidic channel associated with the backplate.

18. The electrode of claim 17 wherein the microfluidic channel is incorporated into a poly-dimethylsiloxane layer of the backplate.

19. The electrode of claim 17 wherein the micro fluidic channel is fabricated into the backplate.

20. The electrode of claim 1 or claim 3 further comprising a microfluidic valve associated with the backplate.

21. The electrode of claim 20 wherein the microfluidic valve is incorporated into a poly-dimethylsiloxane layer of the backplate.

22. The electrode of claim 20 wherein the microfluidic valve is fabricated into the backplate.

23. The electrode of claim 1 or the apparatus of claim 3 wherein the biological membrane is part of a cell.

24. The apparatus of claim 3 further comprising a removable cover.

25. A multiple electrode array comprising a plurality of electrodes according to claim 1, wherein the electrodes are within one or more wells.

26. The multiple electrode array of claim 25 wherein the multiple electrode array comprises 96, 384 or 1536 wells.

27. A method of measuring cell membrane current or cell voltage comprising:
   a). sealing a cell to an apertured-partition of an apparatus used for measuring ionic currents across a biological membrane, said apparatus comprising:
      i).an electrode comprising a silicone polymer molded so as to form a partition comprising an aperture, said apertured-partition capable of forming a high resistance seal of at least 100 MΩ with a biological membrane; and a backplate associated with the apertured-partition, said backplate comprising an electrically conductive contact, wherein the association of the apertured-partition and the backplate forms a first compartment associated with the aperture, said first compartment containing the electrically conductive contact and a first solution; and
      ii). walls associated with the electrode so as to form a chamber, said chamber comprising a second compartment containing a second solution; and
   b). measuring the cell membrane current or cell voltage of the cell sealed to the apertured-partition.

* * * * *